US012636151B2

(12) United States Patent
Quill

(10) Patent No.: US 12,636,151 B2
(45) Date of Patent: *May 26, 2026

(54) DELIVERY SYSTEM WITH ANCHORING NOSECONE AND METHOD OF DELIVERY

(71) Applicant: Medtronic, Inc., Minneapolis, MN (US)

(72) Inventor: Jason Quill, Forest Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 848 days.

This patent is subject to a terminal disclaimer.

(21) Appl. No.: 18/060,142

(22) Filed: Nov. 30, 2022

(65) Prior Publication Data

US 2023/0098390 A1 Mar. 30, 2023

Related U.S. Application Data

(60) Continuation of application No. 16/900,005, filed on Jun. 12, 2020, now Pat. No. 11,534,299, which is a (Continued)

(51) Int. Cl.
*A61F 2/24* (2006.01)
*A61B 17/00* (2006.01)
(Continued)

(52) U.S. Cl.
CPC ........ *A61F 2/2436* (2013.01); *A61B 17/0057* (2013.01); *A61B 17/0401* (2013.01);
(Continued)

(58) Field of Classification Search
CPC .... A61F 2/2436; A61F 2/2418; A61F 2/2457; A61F 2/2466; A61F 2/9517;
(Continued)

(56) References Cited

U.S. PATENT DOCUMENTS

| | | | | |
|---|---|---|---|---|
| 4,960,424 A | * | 10/1990 | Grooters | A61F 2/2457 |
| | | | | 128/898 |
| 5,344,442 A | * | 9/1994 | Deac | A61F 2/2412 |
| | | | | 623/901 |

(Continued)

FOREIGN PATENT DOCUMENTS

| | | |
|---|---|---|
| CN | 1812746 A | 8/2006 |
| WO | 2005000161 A2 | 1/2005 |

(Continued)

OTHER PUBLICATIONS

International Search Report issued in International Application No. PCT/US2018/025864 dated Sep. 20, 2018.

*Primary Examiner* — Sarah W Aleman
*Assistant Examiner* — Rachel S Highland
(74) *Attorney, Agent, or Firm* — MEDLER FERRO WOODHOUSE & MILLS PLLC

(57) ABSTRACT

A delivery device includes an inner shaft, an outer sheath, a nosecone, and a tether component. The outer sheath is slidably disposed over the inner shaft. The nosecone is removably coupled to the inner shaft. The nosecone includes a delivery configuration for delivery to a treatment site, a radially compressed configuration in which a portion of the nosecone is configured to traverse through a heart wall, and a radially expanded configuration in which an outer surface of the nosecone contacts an outer surface of the heart wall. The tether component includes a first end coupled to the nosecone. The nosecone is configured to plug a piercing in the heart wall when in the radially expanded configuration.

17 Claims, 27 Drawing Sheets

Related U.S. Application Data division of application No. 15/479,331, filed on Apr. 5, 2017, now Pat. No. 10,716,668.

(51) Int. Cl.
*A61B 17/04* (2006.01)
*A61F 2/95* (2013.01)

(52) U.S. Cl.
CPC .......... *A61F 2/2418* (2013.01); *A61F 2/2457* (2013.01); *A61F 2/2466* (2013.01); *A61B 2017/00243* (2013.01); *A61B 2017/00247* (2013.01); *A61B 2017/00292* (2013.01); *A61B 2017/00477* (2013.01); *A61B 2017/00575* (2013.01); *A61B 2017/00592* (2013.01); *A61B 2017/00615* (2013.01); *A61B 2017/00619* (2013.01); *A61B 2017/00623* (2013.01); *A61B 2017/00867* (2013.01); *A61B 2017/0409* (2013.01); *A61B 2017/0419* (2013.01); *A61B 2017/0464* (2013.01); *A61F 2/9517* (2020.05)

(58) Field of Classification Search
CPC ............ A61B 17/0057; A61B 17/0401; A61B 2017/00243; A61B 2017/00247; A61B 2017/00292; A61B 2017/00477; A61B 2017/00575; A61B 2017/00592; A61B 2017/00615; A61B 2017/00619; A61B 2017/00623; A61B 2017/00867; A61B 2017/0409; A61B 2017/0419; A61B 2017/0464

See application file for complete search history.

(56) References Cited

U.S. PATENT DOCUMENTS

| | | | |
|---|---|---|---|
| 6,332,893 B1 * | 12/2001 | Mortier | A61F 2/2487 623/2.41 |
| 7,320,665 B2 | 1/2008 | Vijay | |
| 7,621,948 B2 | 11/2009 | Herrmann et al. | |
| 8,105,375 B2 | 1/2012 | Navia et al. | |
| 8,591,460 B2 | 11/2013 | Wilson et al. | |
| 9,078,994 B2 | 7/2015 | Rosenman et al. | |
| 9,211,115 B2 | 12/2015 | Annest et al. | |
| 9,498,330 B2 * | 11/2016 | Solem | A61F 2/246 |
| 2004/0260394 A1 | 12/2004 | Douk et al. | |
| 2005/0075727 A1 * | 4/2005 | Wheatley | A61F 2/2457 623/902 |
| 2007/0088431 A1 | 4/2007 | Bourang et al. | |
| 2007/0270943 A1 | 11/2007 | Solem et al. | |
| 2008/0086164 A1 | 4/2008 | Rowe | |
| 2008/0294251 A1 | 11/2008 | Annest et al. | |
| 2010/0023117 A1 * | 1/2010 | Yoganathan | A61F 2/2457 623/2.37 |
| 2011/0082538 A1 | 4/2011 | Dahigren et al. | |
| 2011/0184439 A1 | 7/2011 | Anderson et al. | |
| 2011/0208297 A1 | 8/2011 | Tuval et al. | |
| 2012/0059458 A1 | 3/2012 | Buchbinder et al. | |
| 2013/0060328 A1 | 3/2013 | Rothstein | |
| 2013/0172978 A1 | 7/2013 | Vidlund et al. | |
| 2013/0184811 A1 | 7/2013 | Rowe et al. | |
| 2013/0226290 A1 | 8/2013 | Yellin et al. | |
| 2013/0231735 A1 | 9/2013 | Deem et al. | |
| 2013/0310928 A1 | 11/2013 | Morriss et al. | |
| 2013/0338764 A1 * | 12/2013 | Thornton | A61B 17/00234 623/2.11 |
| 2014/0039611 A1 | 2/2014 | Lane et al. | |
| 2014/0121763 A1 | 5/2014 | Duffy et al. | |
| 2014/0324161 A1 | 10/2014 | Tegels et al. | |
| 2014/0350669 A1 | 11/2014 | Gillespie et al. | |
| 2014/0358224 A1 * | 12/2014 | Tegels | A61L 27/54 623/2.14 |
| 2014/0379074 A1 | 12/2014 | Spence et al. | |
| 2015/0119981 A1 | 4/2015 | Khairkhahan et al. | |
| 2015/0238315 A1 | 8/2015 | Rabito et al. | |
| 2015/0289975 A1 | 10/2015 | Costello | |
| 2015/0297346 A1 | 10/2015 | Duffy et al. | |
| 2016/0000562 A1 * | 1/2016 | Siegel | A61F 2/2466 623/2.11 |
| 2016/0143736 A1 * | 5/2016 | Vidlund | A61F 2/2418 623/2.4 |
| 2018/0110468 A1 | 4/2018 | Goldshtein et al. | |
| 2018/0289473 A1 | 10/2018 | Rajagopal et al. | |

FOREIGN PATENT DOCUMENTS

| | | | |
|---|---|---|---|
| WO | 2011/051942 A1 | 5/2011 | |
| WO | 2013/011502 A2 | 1/2013 | |
| WO | 2014/159754 A2 | 10/2014 | |
| WO | 2016178196 A2 | 11/2016 | |

* cited by examiner

DELIVERY SYSTEM WITH ANCHORING NOSECONE AND METHOD OF DELIVERY

CROSS-REFERENCE TO RELATED APPLICATION

This application is a continuation of U.S. application Ser. No. 16/900,005, filed Jun. 12, 2020, which is a divisional of U.S. application Ser. No. 15/479,331, filed Apr. 5, 2017, now U.S. Pat. No. 10,716,668, each of which is hereby incorporated by reference in its entirety for all purposes.

FIELD OF THE INVENTION

The present invention relates to systems and methods for deploying a stented prosthetic heart valve at the site of a native valve. More particularly, the present invention relates to a delivery system with a nosecone plug and tethers for anchoring a stented prosthetic mitral valve within an annulus of a native mitral valve.

BACKGROUND OF THE INVENTION

Heart valves are sometimes damaged by disease or by aging, resulting in problems with the proper functioning of the valve. Heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter delivery and implantation of replacement cardiac valves to solve the problems presented by traditional open surgery and minimally invasive surgical methods. In such methods, a stented prosthetic heart valve, also known generally as a valve prosthesis, is compacted for delivery in a catheter and then advanced, for example through an opening in the femoral artery, through the inferior vena cava, through the interatrial septum, where the stented prosthetic heart valve is then deployed in the annulus of the native heart valve.

Various types and configurations of stented prosthetic heart valves are available for percutaneous valve replacement procedures. In general, stented prosthetic heart valve designs attempt to replicate the function of the heart valve being replaced and thus will include valve leaflet-like structures. Stented prosthetic heart valves, also known as valve prostheses, are generally formed by attaching a bioprosthetic valve to a frame made of a wire or a network of wires. Such a stented prosthetic heart valve can be collapsed radially to introduce the stented prosthetic heart valve into the body of the patient percutaneously through a catheter. The stented prosthetic heart valve may be deployed by radially expanding it once positioned at the desired deployment site. If the deployed valve prosthesis is incorrectly positioned relative to the annulus of the native heart valve or migrates once radially expanded, serious complications may arise, including paravalvular leakage (PVL) or the requirement for placement of a permanent pacemaker. Mitral valve replacement is especially susceptible to stented prosthetic valve migration due to the native anatomy of the heart.

Accordingly, there is a need for systems and methods to more easily position and anchor a stented prosthetic heart valve in the annulus of a native heart valve.

BRIEF SUMMARY OF THE INVENTION

Embodiments hereof relate to a delivery device including an inner shaft, an outer sheath, a nosecone, and a tether component. The outer sheath is slidably disposed over the inner shaft. The nosecone is removably coupled to the inner shaft. The nosecone includes a radially compressed configuration and a radially expanded configuration. A portion of the nosecone is configured to traverse through a heart wall when in the radially compressed configuration. The nosecone is configured such that an outer surface of the nosecone contacts an outer surface of the heart wall when in the radially expanded configuration. The tether component includes a first end coupled to the nosecone.

Embodiments hereof also relate to a delivery system including a catheter, a prosthesis, and a tether component. The catheter includes an inner shaft, an outer sheath, and a nosecone. The outer sheath is disposed about the inner shaft. The nosecone is removably coupled to the inner shaft. The prosthesis includes a radially collapsed configuration and a radially expanded configuration. The prosthesis is configured to be disposed within the outer sheath when in the radially collapsed configuration. The tether component includes a first end coupled to the nosecone and a second end coupled to the prosthesis. The nosecone is configured to anchor the prosthesis to a heart wall with the tether component.

Embodiments hereof also relate to a method of deploying a prosthesis at a site of a native valve. A delivery system includes an outer sheath, a nosecone removably coupled to the delivery system, and a prosthesis disposed within the outer sheath in a radially collapsed configuration. The delivery system is advanced through the native valve and into a chamber of a heart. A portion of the nosecone is advanced through the wall of the heart with the nosecone in a radially compressed configuration. The delivery system is retracted such that an outer surface of the nosecone contacts an outer surface of the heart wall and the nosecone expands to a radially expanded configuration. The nosecone is released from the delivery system. The delivery system is retracted until the tether component becomes taut. The outer sheath is retracted to release the prosthesis such that the prosthesis expands to a radially expanded configuration at the site of the native valve.

DETAILED DESCRIPTION OF THE
INVENTION

Specific embodiments of the present invention are now described with reference to the figures, wherein like reference numbers indicate identical or functionally similar elements. The terms "distal" and "proximal", when used in the following description to refer to a delivery device or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a device to be implanted into a vessel, such as a stented prosthetic heart valve, also known generally as a valve prosthesis, or a docking stent, are used with reference to the direction of blood flow from the heart. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1B:
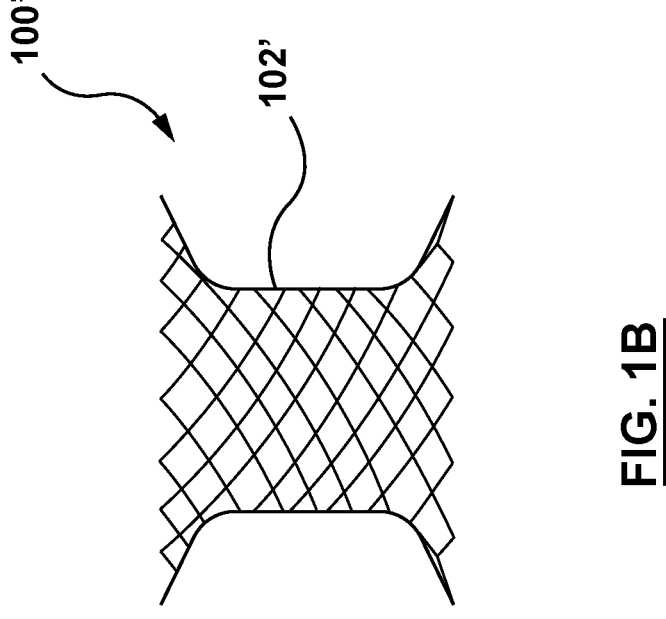
FIG. 1B is a schematic illustration of a docking stent according to another embodiment hereof.
Figure 1A:
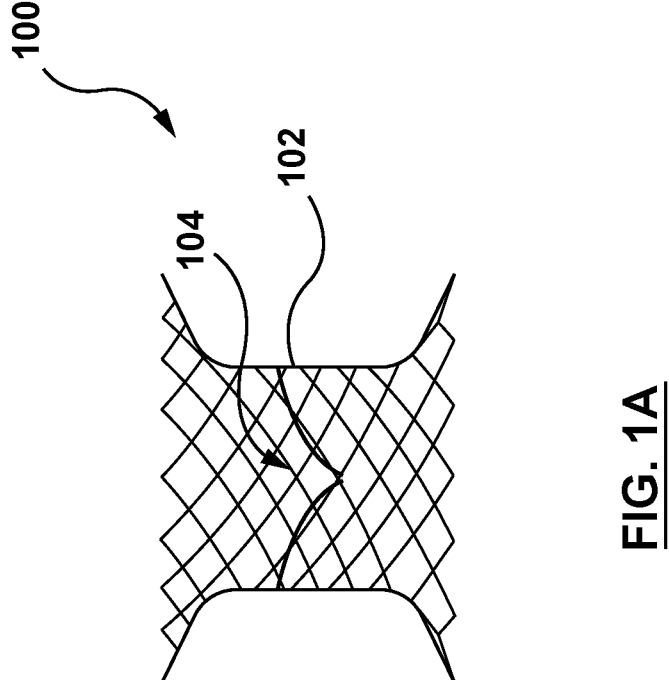
FIG. 1A is a schematic illustration of a stented prosthetic heart valve according to an embodiment hereof.

The present invention in various embodiments relate to a delivery system for delivering, deploying, and anchoring a prosthesis at a site of a native valve. The prosthesis to be anchored may be a stented prosthetic heart valve 100, also referred to herein as a valve prosthesis, as shown in an embodiment shown in FIG. 1A. Stented prosthetic heart valve 100 includes a frame 102 supporting a valve component or structure 104. Valve structure 104 of stented prosthetic heart valve 100 includes leaflets configured for replacing leaflets of a native heart valve and the leaflets may be constructed from tissue and/or synthetic materials. For example, stented prosthetic heart valve 100 useful with the present disclosure can be a prosthesis sold under the trade name CoreValve® available from Medtronic CoreValve, LLC, as described in U.S. Pat. No. 8,226,710 to Nguyen, incorporated by reference herein in its entirety. Alternatively, the prosthesis to be anchored may be a docking stent as shown in FIG. 1B. Docking stent 100' includes a frame 102'. Both stented prosthetic heart valve 100 and docking stent 100' have a radially expanded configuration (when deployed) that is collapsible to a radially collapsed configuration for loading within an outer sheath of a delivery device. Frames 102, 102' are constructed from a self-expanding material that is configured to self-deploy or expand when released from the delivery device (catheter) at the site of a native valve. Frames 102, 102' are generally tubular support structures that comprises a number of struts or wire portions arranged relative to each other to provide a desired compressibility and strength to stented prosthetic valve 100, docking stent 100', respectively. As used herein in the description and the claims, the term "prosthesis" is used to collectively refer to either a stented prosthetic heart valve or a docking stent.

A delivery system in accordance with the embodiments hereof includes a delivery device or catheter and a prosthesis (e.g., stented prosthetic valve 100 or docking stent 100' described above) mounted at a distal portion of the delivery device. The delivery device generally includes an inner shaft, an outer sheath, a nosecone, and a tether component. The nosecone is removably coupled to the inner shaft. The nosecone is configured to anchor the prosthesis to a heart wall utilizing the tether component. More specifically, the nosecone, or a portion thereof, is configured to traverse the heart wall in a radially compressed configuration and to expand to a radially expanded configuration after traversing the heart wall. Once in the radially expanded configuration, the nosecone is configured to anchor against an outer surface of the heart wall. The delivery system is configured to release the prosthesis from a radially collapsed configuration to a radially expanded configuration at the site of the native valve. The tether component is configured to be taut when the prosthesis is properly positioned within the native valve. The nosecone is configured to function as an anchor that secures the prosthesis to the heart wall via the tether component.

Figure 2:
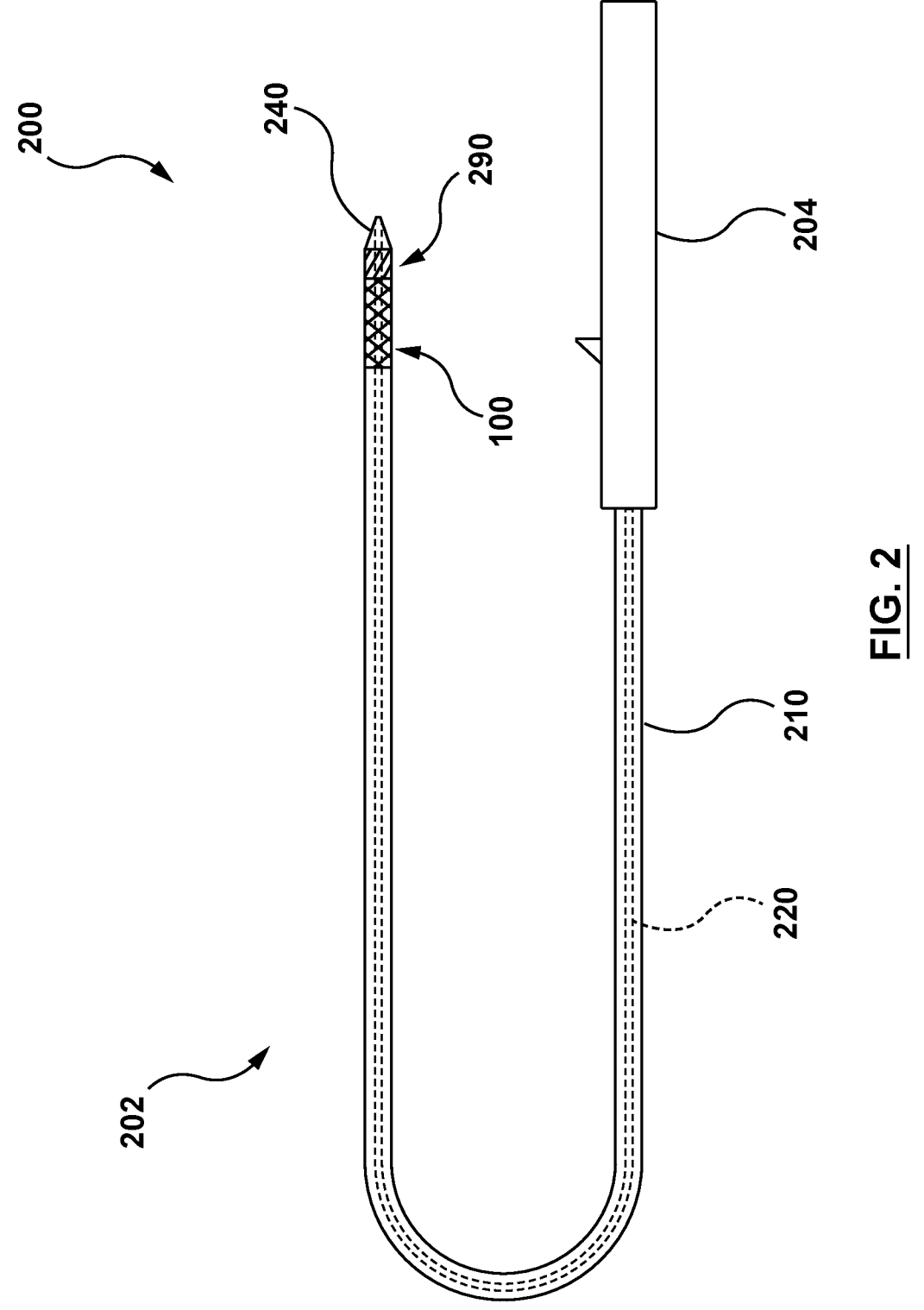
FIG. 2 is a side view illustration of a delivery system according to an embodiment hereof, wherein the stented prosthetic heart valve of FIG. 1A is mounted at a distal portion thereof and the stented prosthetic heart valve is shown in its radially collapsed configuration for delivery.

In an embodiment shown in FIG. 2 and in greater detail in FIGS. 3-15, a delivery system 200 includes a delivery device or catheter 202 and stented prosthetic heart valve 100 mounted on a distal portion thereof for delivery. Delivery device 202 is configured to deliver and implant stented prosthetic heart valve 100 according to an embodiment of the present invention. Stented prosthetic heart valve 100 has a radially collapsed configuration for delivery and a radially expanded configuration when deployed at a desired deployment location. In the embodiment shown in FIG. 2, delivery system 200 is shown delivering and deploying stented prosthetic heart valve 100 but as described above delivery system 200 may also be utilized for delivering and deploying other prostheses including but not limited to docking stent 100'.

Delivery device 202 includes a hub or handle 204, an outer sheath 210, an inner shaft 220, a nosecone 240, and a tether component 290, as shown in FIG. 2. Components of delivery device 202 may assume different forms and construction based upon application needs as described in greater detail in U.S. Pat. No. 7,662,186 to Bragga and U.S. Pat. No. 7,740,655 to Birdsall, each of which is incorporated in their entirety by reference herein.

Figure 3:
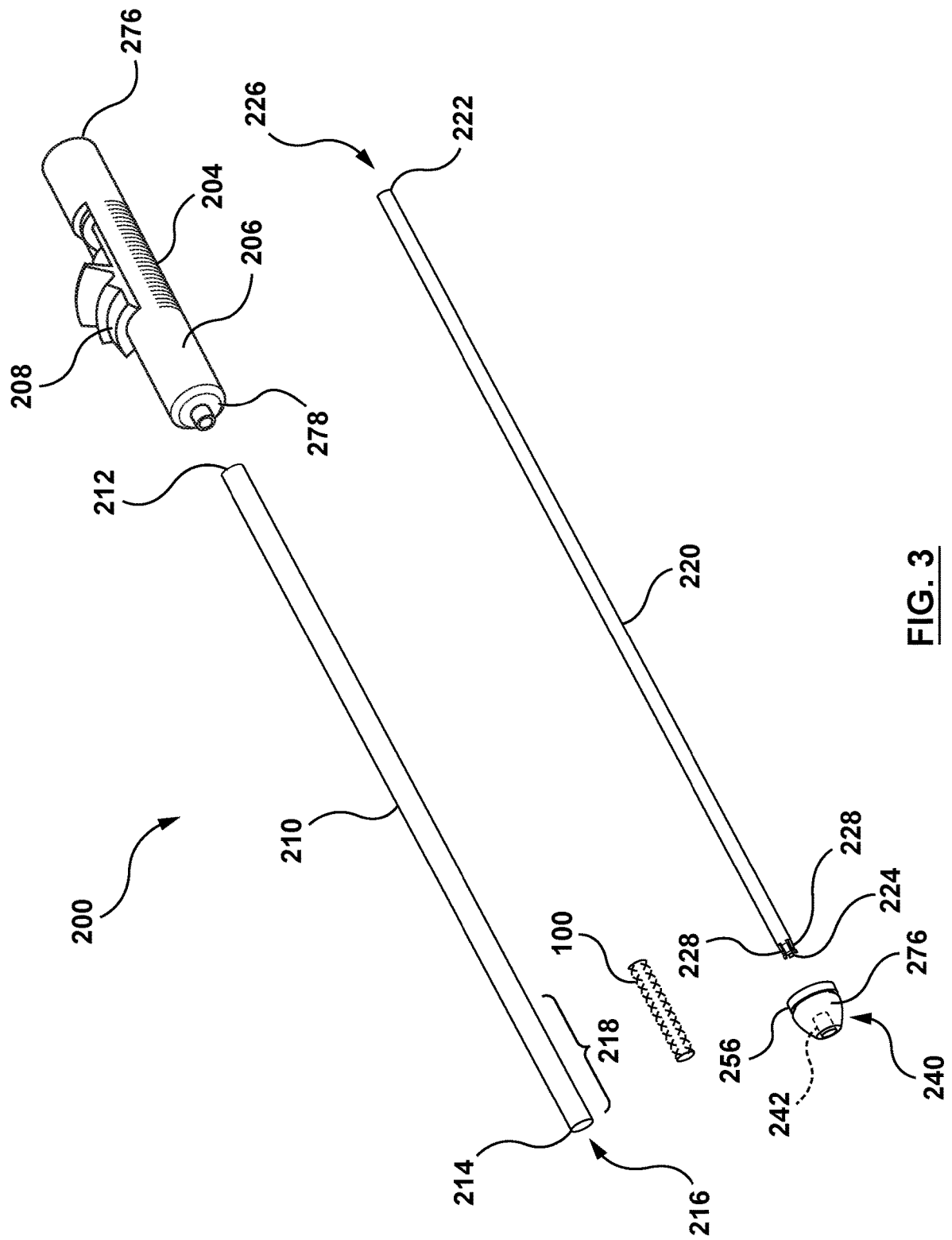
FIG. 3 is an exploded perspective illustration of the delivery system of FIG. 2.

As shown in FIG. 3, handle 204 includes a housing 206 and a retraction mechanism 208 retained therein. Handle 204 is configured such that retraction mechanism 208 extends through housing 206 for interfacing by a user. Handle 204 provides a surface for convenient handling and grasping by a user, and can have a generally cylindrical shape. While handle 204 is shown with a cylindrical shape, is not meant to limit design, and other shapes and sizes may be utilized. Handle 204 can assuming a variety of configurations described in greater detail U.S. Pat. No. 8,579,963 to Tabor, incorporated in its entirety by reference herein.

As also shown in FIG. 3, outer sheath 210 of delivery system 200 includes a proximal end 212 and a distal end 214. Outer sheath 210 defines a lumen 216 sized to receive inner shaft 220 therethrough. Outer sheath 210 further includes a distal portion 218 configured to retain stented prosthetic heart valve 100 in its radially collapsed configuration therein. Outer sheath 210 is coaxially and slidably disposed over inner shaft 220. Although outer sheath 210 is described herein as a single component, this is not meant to limit the design and outer sheath 210 may include components such as, but not limited to a proximal shaft, a capsule, or other components suitable for the purposes described herein. Outer sheath 210 extends proximally into housing 206 of handle 204 and a proximal portion of outer sheath 210 is rigidly connected to retraction mechanism 208 of handle 204. The proximal portion of outer sheath 210 is coupled to retraction mechanism 208 such that movement of retraction mechanism 208 causes outer sheath 210 to move relative to inner shaft 220. Outer sheath 210 is thus movable relative to handle 204 and inner shaft 220 by retraction mechanism 208. However, if retraction mechanism 208 is not moved and handle 204 is moved, outer sheath 210 moves with handle 204, not relative to handle 204. Outer sheath 210 may be constructed of materials such as, but not limited to polyurethane (e.g. Peliethane©, Elasthane™, Texin®, Tecothane®), polyamide polyether block copolymer (e.g. Pebax®, nylon 12), polyethylene, or other materials suitable for the purposes of the present disclosure. Outer sheath 210 may be coupled to retraction mechanism 208, for example, and not by way of limitation by adhesives, welding, clamping, and other coupling methods as appropriate.

As also shown in FIG. 3, inner shaft 220 extends from a proximal end 222 to a distal end 224, inner shaft 220 defining a lumen 226 sized to receive a guidewire (not shown in FIG. 3) and/or a needle tube (not shown in FIG. 3) therethrough. Inner shaft 220 further defines a plurality of legs 228 at distal end 224 for coupling inner shaft 220 to nosecone 240 as will be described in more detail herein. Although inner shaft 220 is described herein as a single component, this is not meant to limit the design and inner shaft 220 may include components such as, but not limited to a proximal shaft, a retention member, or other components suitable for the purposes described herein. Inner shaft 220 extends proximally through housing 206 of handle 204, and is rigidly connected to handle 204 such that lumen 226 provides access for auxiliary components (e.g., a guidewire, a needle tube) therein. During sliding or longitudinal movement of outer sheath 210 relative thereto, inner shaft 220 is fixed relative to handle 204, as shown in FIG. 3. Inner shaft 220 may be coupled to handle 204, for example, and not by way of limitation, by adhesives, welding, clamping, and other coupling devices as appropriate. Inner shaft 220 can assume a variety of configurations described in greater detail in U.S. Pat. No. 8,579,963 to Tabor, previously incorporated by reference herein.

Figure 4:
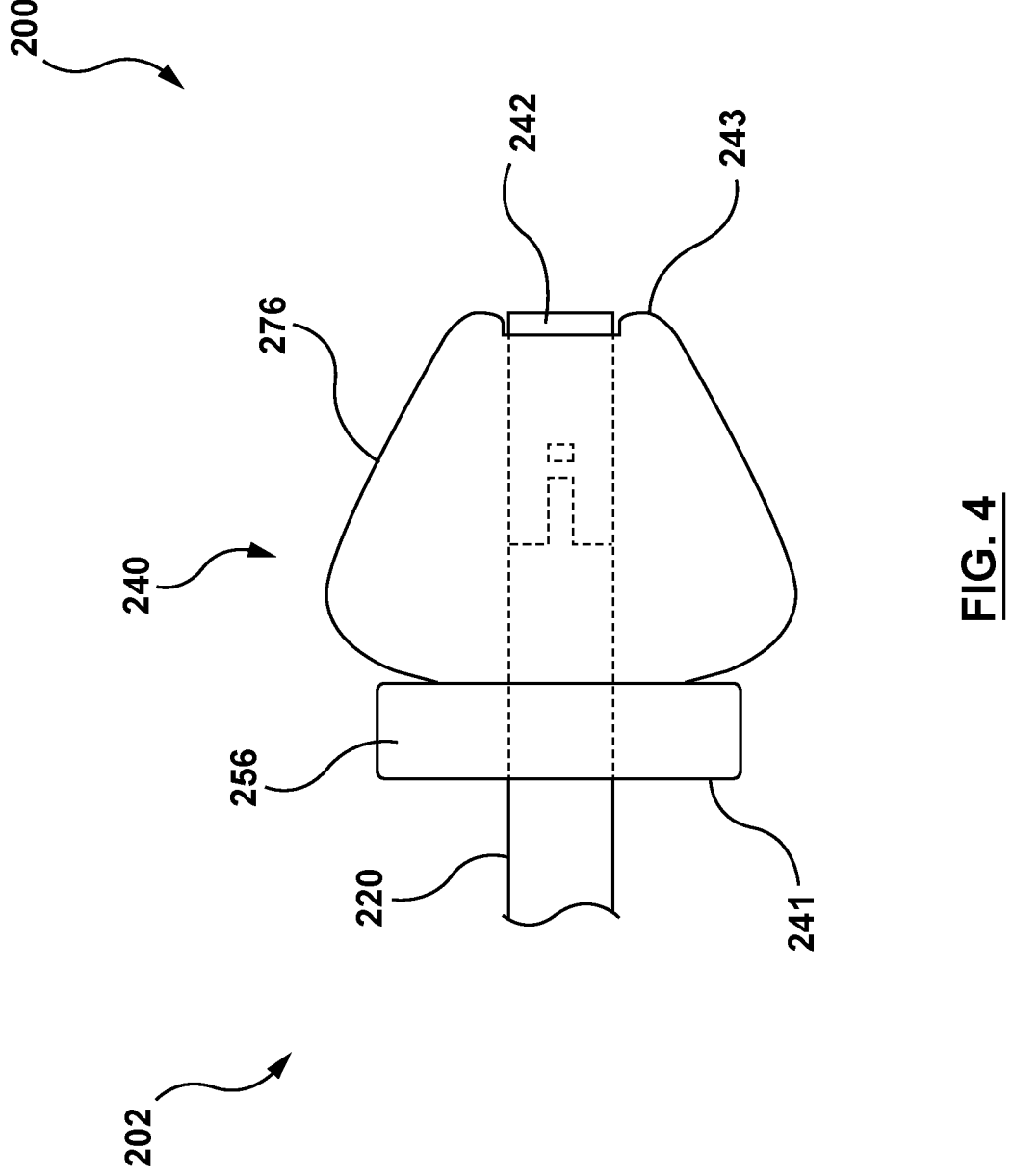
FIG. 4 is a side view illustration of a nosecone of the delivery system of FIG. 2 wherein the nosecone is in its delivery configuration.

As shown in FIG. 3 and in greater detail in FIG. 4, nosecone 240 includes an inner member 242, a retainer 256, and a nosecone plug 276. Nosecone 240 further includes a proximal end 241 and a distal end 243. Nosecone 240 is configured to be removably coupled to distal end 224 of inner shaft 220, as described in greater detail below. Nosecone 240 is further configured to anchor stented prosthetic heart valve 100 to a heart wall with tether component 290 (not shown in FIG. 3 or 4), as described in greater detail below. Nosecone 240 has a delivery configuration shown in FIG. 5 for advancement through the vasculature of a patient and delivery to a desired deployment site. A proximal portion 245 of nosecone plug 276 has a cross-sectional dimension $CD_{ND}$ when nosecone 240 is in the delivery configuration of FIG. 5. Nosecone 240 further includes a radially compressed configuration shown in FIG. 6, with a distal portion 247 of nosecone 240 configured to traverse through a heart wall. When nosecone 240 is in the radially compressed configuration of FIG. 6, proximal portion 245 of nosecone plug 276 has a cross-sectional dimension $CD_{NC}$. Cross-sectional dimension $CD_{ND}$ (when nosecone 240 is in the delivery configuration of FIG. 5) is larger than cross-sectional dimension $CD_{NC}$ (when nosecone 240 is in the radially collapsed configuration of FIG. 6). Nosecone 240 further includes a radially expanded configuration shown in FIG. 7, wherein an outer surface 277 of the nosecone plug 276 of nosecone 240 contacts an outer surface of the heart wall HW. Proximal portion 245 of nosecone plug 276 has a cross-sectional dimension $CD_{NE}$ when nosecone 240 is in the radially expanded configuration of FIG. 7. Cross-sectional dimension $CD_{NE}$ (when nosecone 240 is in the radially expanded configuration of FIG. 7) is larger than cross-sectional dimension $CD_{ND}$ (when nosecone 240 is in the delivery configuration of FIG. 5). When in the radially expanded configuration of FIG. 7, the nosecone 240 is additionally configured to plug a piercing in the heart wall HW and to anchor or secure stented prosthetic heart valve 100 at the desired deployment location as will be described in greater detail below. Nosecone 240 is formed in its delivery configuration of FIG. 5, and force is applied thereto in order to transition or transform it into the radially collapsed configuration of FIG. 6 and in order to transition or transform it into the radially expanded configuration of FIG. 7.

Figures 8, 9:
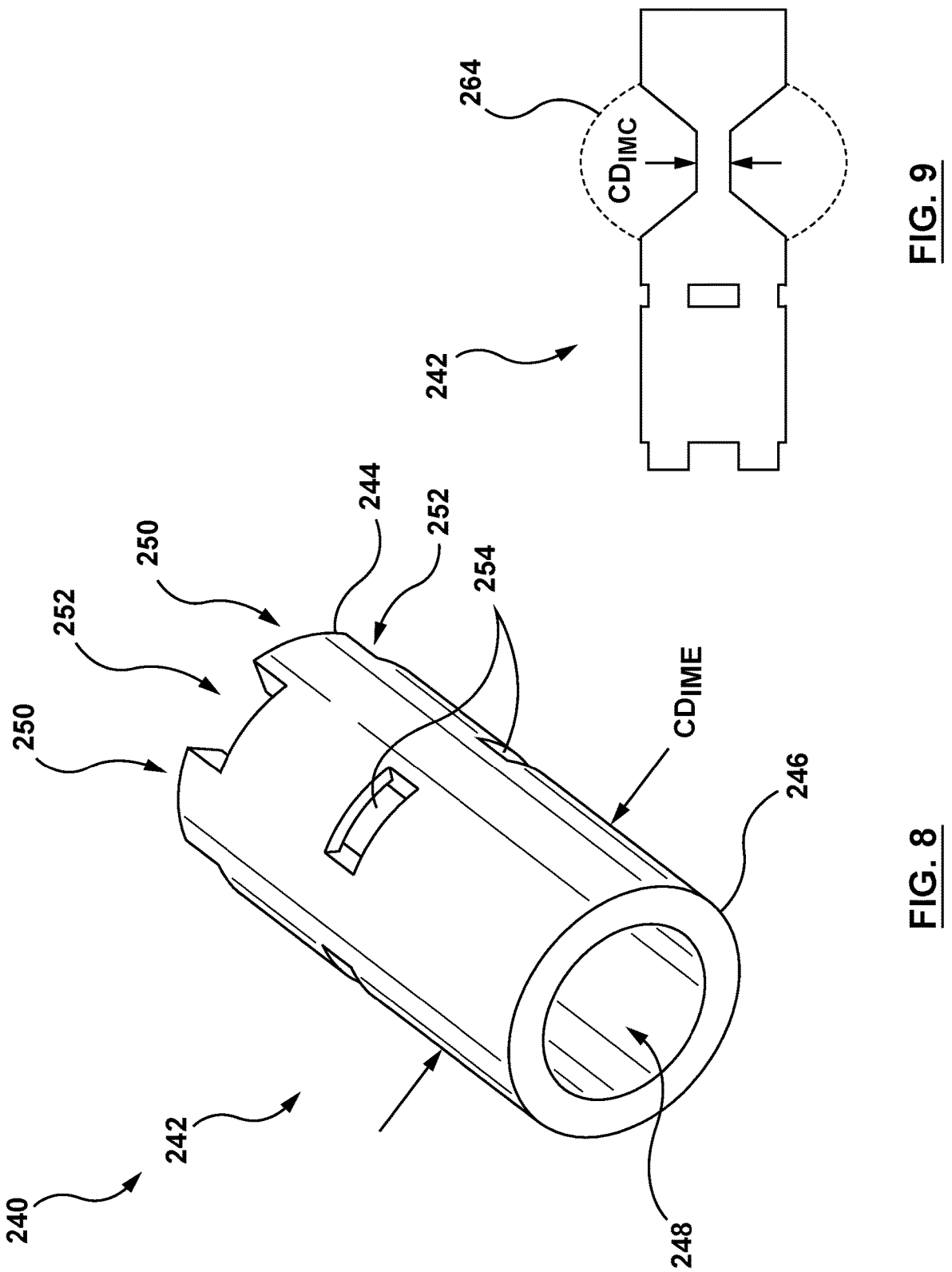
FIG. 8 is a perspective illustration of an inner member of the nosecone of FIG. 4, wherein the inner member is in its expanded state.
FIG. 9 is a side view illustration of the inner member of the nosecone of FIG. 4, wherein the inner member is in its expanded state.

The components of nosecone 240 will now be described in more detail in turn. As best shown in FIG. 8, inner member 242 of nosecone 240 is a generally tubular component. Inner member 242 includes a proximal end 244 and a distal end 246, inner member 242 defining a lumen 248. Lumen 248 is sized to receive a guidewire (not shown in FIG. 8) and/or a needle tube (not shown in FIG. 8) therethrough. Distal end 246 of inner member 242 is coupled to a distal end of nosecone plug 276, as shown on FIG. 4 at distal end 243 of nosecone 240. Additionally, proximal end 244 of inner member 242 is removably coupled to distal end 224 of inner shaft 220, as described in greater detail below. Inner member 242 further defines a plurality of legs 250, a plurality of gaps 252, and a plurality of slots 254. Inner member 242 has a radially expanded state, as shown in FIG. 8. Inner member 242 is further configured to be collapsible upon application of a sufficient compressive radial force thereon to a radially collapsed state shown in FIG. 9. When in the radially expanded state of FIG. 8, inner member 242 has a cross-sectional dimension $CD_{IME}$. Inner member 242 is shown in FIG. 9 with a portion of inner member 242 in the radially collapsed state with a cross-sectional dimension $CD_{IMC}$. Cross-sectional dimension $CD_{IME}$ is greater than cross-sectional dimension $CD_{IMC}$. More particularly, inner member 242 is configured to be retracted in a proximal direction such that inner member 242 is proximally retracted into an O-ring 264 of retainer 256. When retracted therein, a portion of inner member 242 collapses, transitioning a portion of inner member 242 from the radially expanded state to the radially collapsed state with cross-sectional dimension $CD_{IMC}$, which is smaller than a cross-sectional dimension $CD_{OE}$ of O-ring 264 (shown in phantom in FIG. 9). After a portion of inner member 242 collapsed to a cross-sectional dimension $CD_{IMC}$ passes though O-ring 264, the collapsed portion of inner member 242 recoils to the radially expanded state with cross-sectional dimension $CD_{IME}$. Accordingly, inner member 242 is constructed of a shape memory material with a pre-set shape in the radially expanded state. Inner member 242 may be constructed of materials such as, but not limited to polyurethane (e.g. Peliethane©, Elasthane™, Texin®, Tecothane®), polyamide polyether block copolymer (e.g. Pebax®, nylon 12), polyethylene, or other materials suitable for the purposes of the present disclosure. While described herein as a single component, inner member 242 may alternatively be formed of individual components coupled together by various methods including, but not limited to welding, adhesives, or other methods suitable for the purposes described herein.

Each leg 250 of inner member 242 is separated from each adjacent leg 250 by a gap 252, as shown in FIG. 8. Each leg 250 is configured to be received within a corresponding gap 230 of inner shaft 220, shown in FIG. 10 and as described in greater detail below. Further, each gap 252 of inner member 242 in FIG. 8 is configured to receive a corresponding proximal portion of each leg 228 of inner shaft 220, shown in FIG. 10. Each slot 254 of inner member 242 is a generally rectangular box shape extending from an outer surface to an inner surface of inner member 242 such that each slot 254 provides access from lumen 248 to an outer surface of inner member 242, as shown in FIG. 8. Stated another way, each slot 254 is a cut-out opening formed through a sidewall of inner member 242 to provide access to lumen 248 of inner member 242. Each slot 254 is disposed distal of and aligned longitudinally with each gap 252. Each slot 254 of FIG. 8 is configured to receive a corresponding tab 231 of a corresponding leg 228 of inner shaft 220, shown in FIG. 10, as described in greater detail below.

Figure 10:
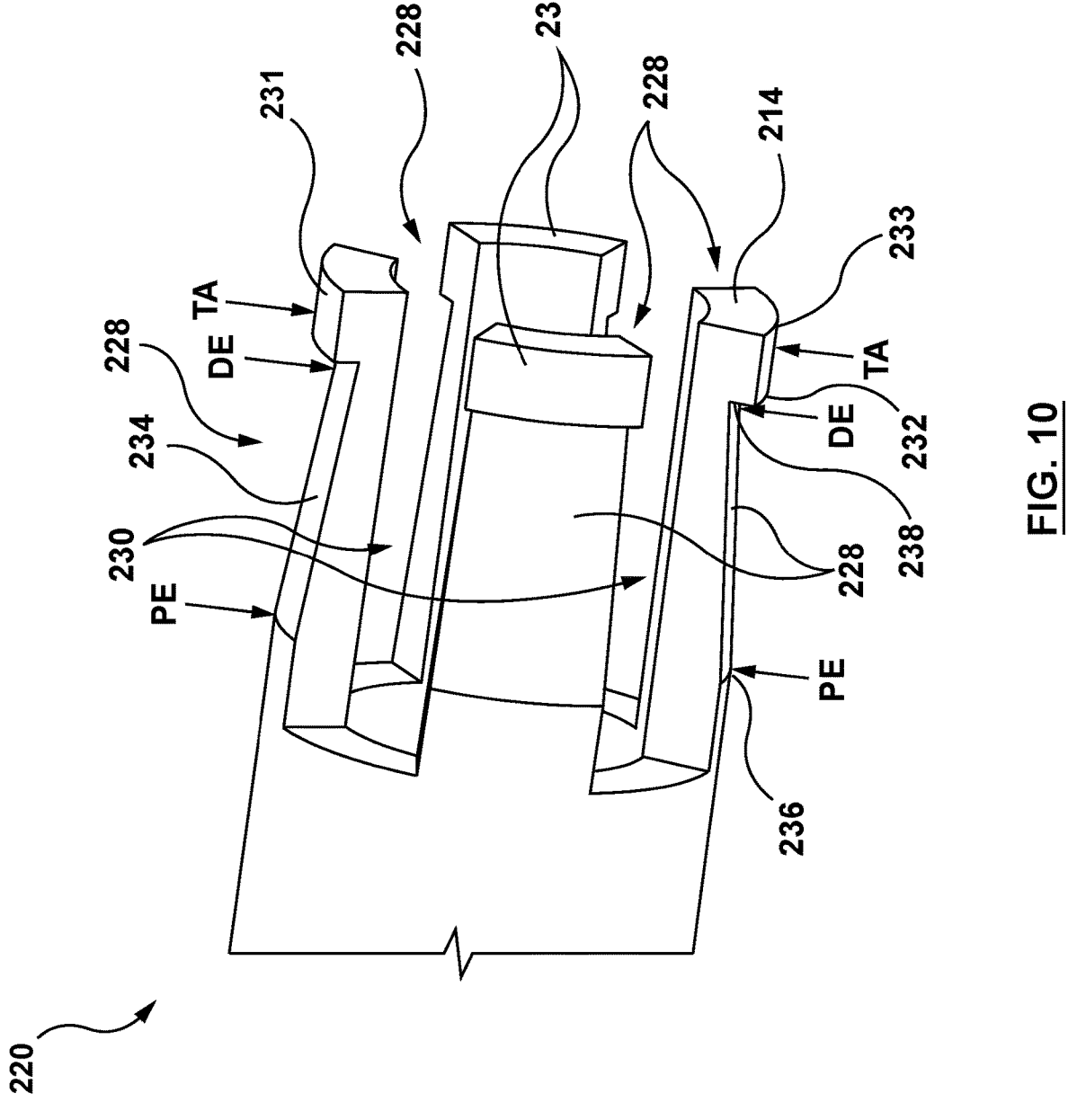
FIG. 10 is a perspective illustration of the distal end of an inner shaft of the delivery system of FIG. 2.

With an understanding of the construction of inner member 242 of nosecone 240, it is now possible to describe an embodiment of the distal portion of inner shaft 220 that is removably coupled thereto. Referring now to FIG. 10, each leg 228 of inner shaft 220 is separated from each adjacent leg 228 by a gap 230. Each leg 220 includes a tapered portion 234 and a tab 231 at a distal end of each tapered portion 234. Each leg 228 is configured to be received within a corresponding gap 252 of inner member 242 of nosecone 240, shown in FIG. 8. Each gap 230 of inner shaft 220 of FIG. 10 is configured to receive a corresponding leg 250 of inner member 242 of nosecone 240. The plurality of legs 228 of inner shaft 220 are configured to removably couple inner shaft 220 to nosecone 240 as described in greater detail below.

Each tapered portion 234 is a generally rectangular shape with a tapered outer surface, as shown in FIG. 10. Each tapered portion 234 includes a proximal end 236 and a distal end 238. The taper of each tapered section 228 begins at proximal end 236 tapering radially inward to distal end 238 such that a cross-sectional dimension PE at proximal end 236 is greater than a cross-sectional dimension DE at distal end 238. Each tapered portion 228 is configured to operate with retainer 256 of nosecone 240, shown in FIG. 4, to provide user actuated release of nosecone 240 from inner shaft 220 as described in greater detail below. Each tapered portion 234 is disposed proximal of each tab 231 of each leg 228, as shown in FIG. 10. Each tapered portion 234 may be constructed of materials such as, but not limited to polyure-thane (e.g. Peliethane©, Elasthane™, Texin®, Tecothane®), polyamide polyether block copolymer (e.g. Pebax®, nylon 12), polyethylene, or other materials suitable for the purposes of the present disclosure. Each tapered portion 234 may be formed for example, and not by way of limitation, as an integral portion of each leg 228 or a separate unit coupled to each leg 228 by for example, and not by way of limitation, fusing, welding, or other methods suitable for the purposes described herein.

Each tab 231 is of a generally rectangular box shape including a proximal end 232 and a distal end 233, as shown in FIG. 10. Each tab 231 is disposed at distal end 238 of each tapered portion 234 of each leg 228. Each tab 231 is configured to removably engage a corresponding slot 254 of inner member 242 of nosecone 240, shown in FIG. 8 and described in greater detail below. Each tab 231 includes an outer surface extending radially outward from each tapered portion 234, as shown in FIG. 10, such that a cross-sectional dimension TA of tabs 231 is greater than the cross-sectional dimension DE of distal end 238 of tapered portion 234. Each tab 231 may be constructed of materials such as, but not limited to polyurethane (e.g. Peliethane©, Elasthane™, Texin®, Tecothane®), polyamide polyether block copoly-mer (e.g. Pebax®, nylon 12), polyethylene, or other mate-rials suitable for the purposes of the present disclosure. Each tab 231 may be formed for example, and not by way of limitation, as an integral portion of each leg 228 or each tapered portion 234, or a separate unit coupled to each leg 228 by for example, and not by way of limitation, fusing, welding, or other methods suitable for the purposes described herein.

Figure 11:
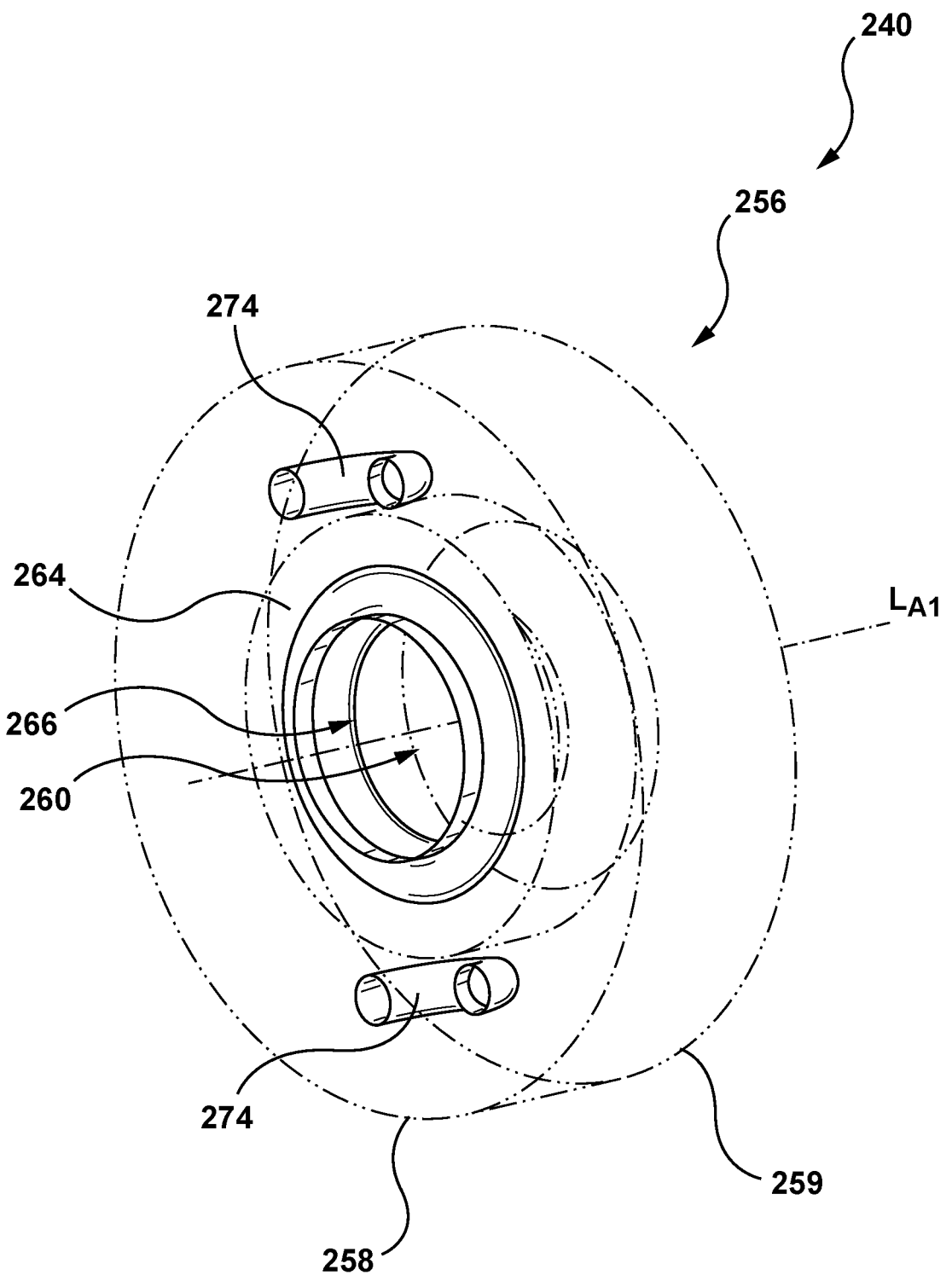
FIG. 11 is a perspective illustration of a retainer of the nosecone of FIG. 4
Figure 12:
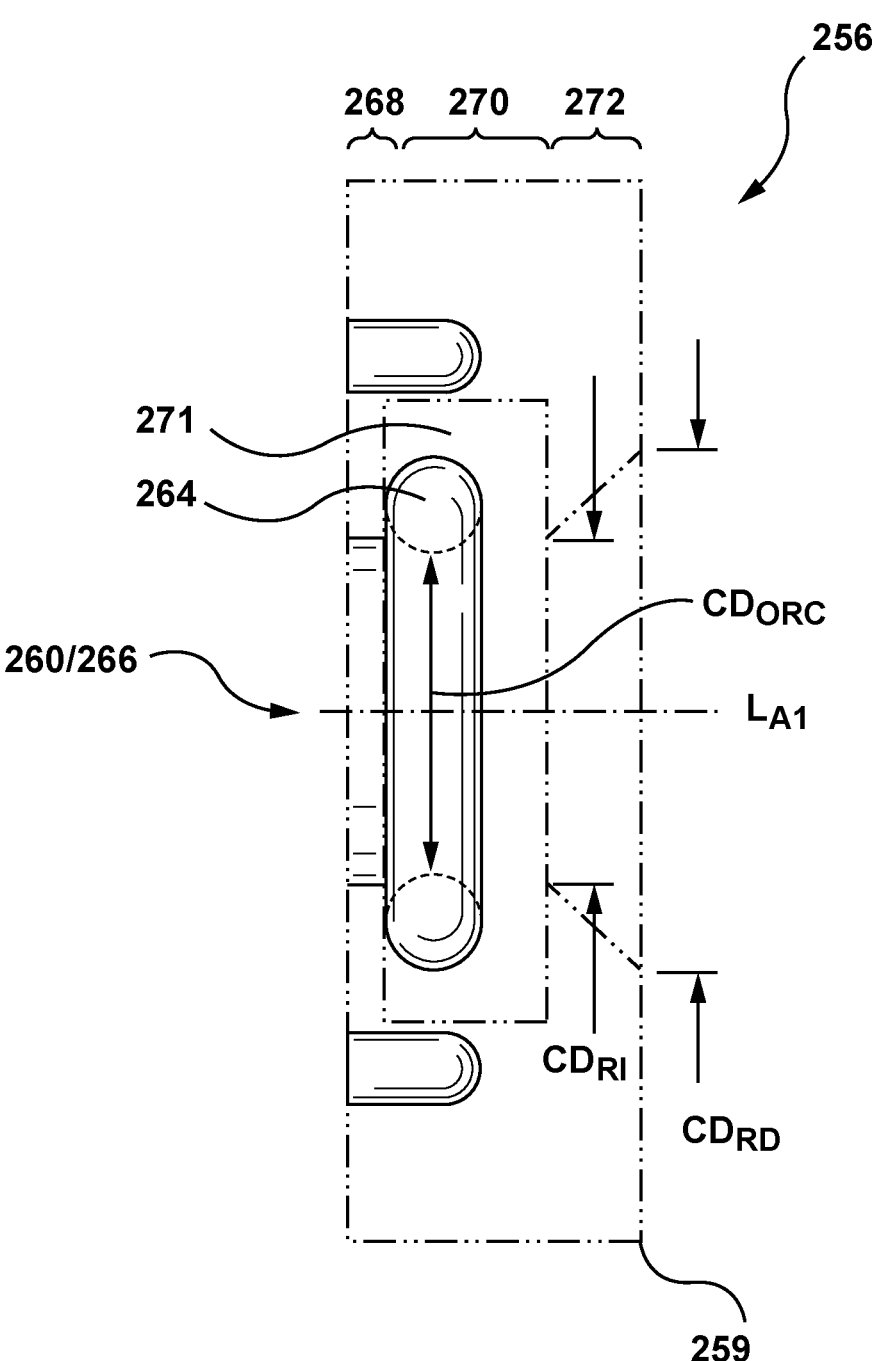
FIG. 12 is a side view illustration of the retainer of FIG. 11.

Retainer 256 of nosecone 240 is shown in FIG. 4 and in greater detail in FIGS. 11-12. Retainer 256 is a general ring or annular shape and includes a proximal end 258 and a distal end 259, as shown in FIG. 11. Retainer 256 defines a lumen 260, configured to receive a distal portion of inner shaft 220 and/or inner member 242 of FIGS. 8-9 there-through. Retainer 256 further includes O-ring 264 and a plurality of tether channels 274. Retainer 256 with O-ring 264, in conjunction with inner shaft 220 and inner member 242, shown in FIG. 4, are configured to removably couple inner nosecone 240 and inner shaft 220, as described in greater detail below. Retainer 256 may be a machined or molded rigid or semi-rigid component formed for example, and not by way of limitation, of stainless steel, Nitinol, thermal-formed plastic or any other material suitable for the purposes described herein.

Retainer 256 further includes a proximal portion 268, a central portion 270, and a distal portion 272, as shown in the side view of FIG. 12. Central portion 270 is disposed between proximal portion 268 and distal portion 272 such that proximal portion 268, central portion 270, and distal portion 272 collectively form continuous lumen 260 of retainer 256. Proximal portion 268 defines a proximal por-tion of lumen 260. Proximal portion 268 is configured to receive a distal portion of inner shaft 220 and/or a portion of inner member 242, as shown in FIG. 4, therethrough. Central portion 270 defines a central portion of lumen 260, as shown in FIG. 12. Central portion 270 also defines a cavity 271 configured to receive O-ring 264 therein, as will be described in greater detail below. Distal portion 272 defines a distal portion of lumen 260, which flares in a distal direction. Due to the flare of the distal portion of lumen 260, distal portion 272 may be described as including a funnel shape with a cross-sectional dimension $CD_{RD}$ of lumen 260 at a distal end of distal portion 272 (co-located with distal end 259 of retainer 256) being greater than a cross-sectional dimension $CD_{RI}$ at a proximal end of distal portion 272. Distal portion 272 is configured to provide convenient retraction of inner member 242 (not shown in FIG. 12) and a proximal portion of nosecone plug 276 (not shown in FIG. 12) therethrough.

Figure 13:
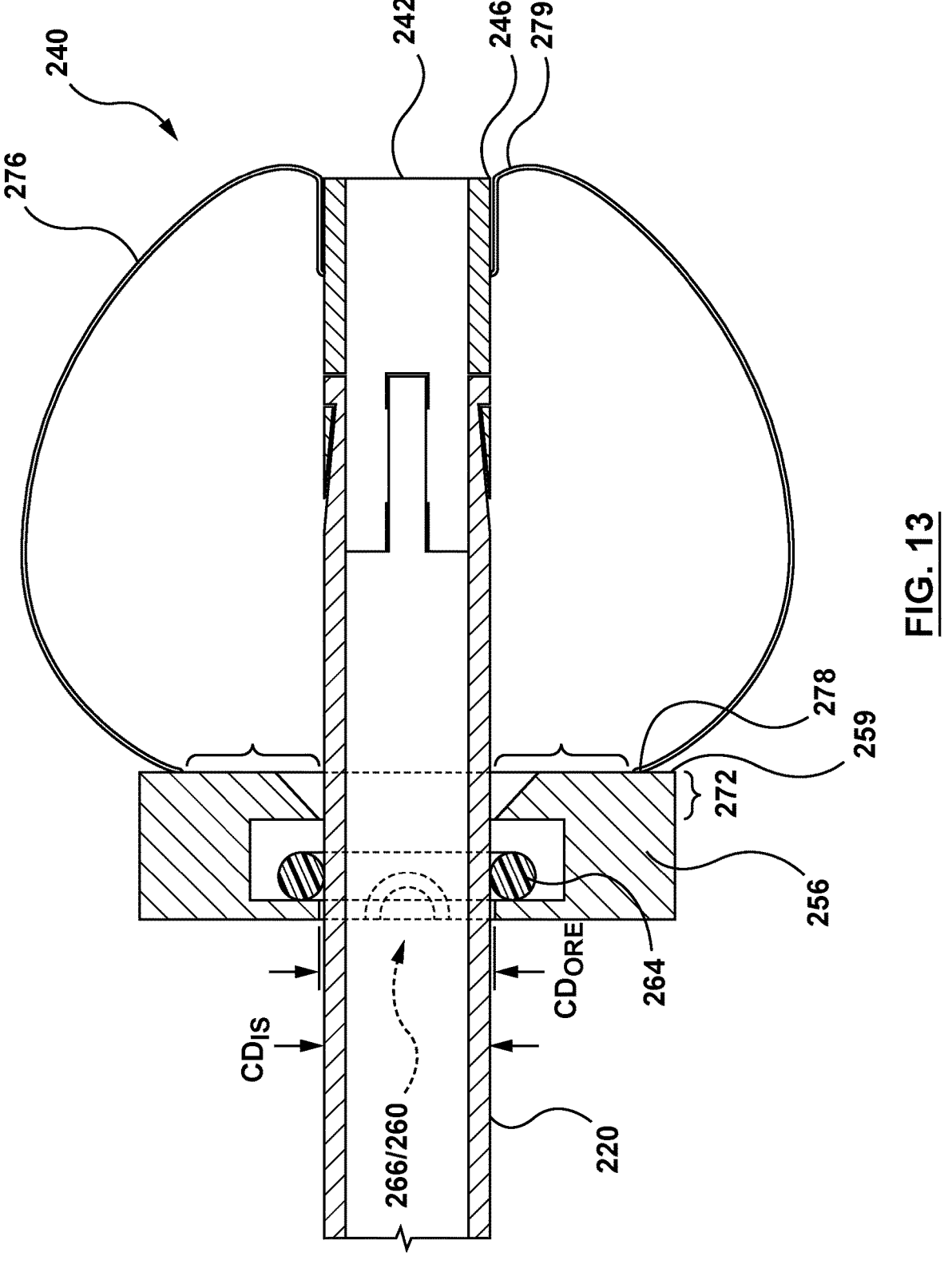
FIG. 13 is a side view illustration of the nosecone and a distal end of the inner shaft of the delivery system of FIG. 2, wherein the nosecone and the distal end of the inner shaft are coupled together.
Figure 14:
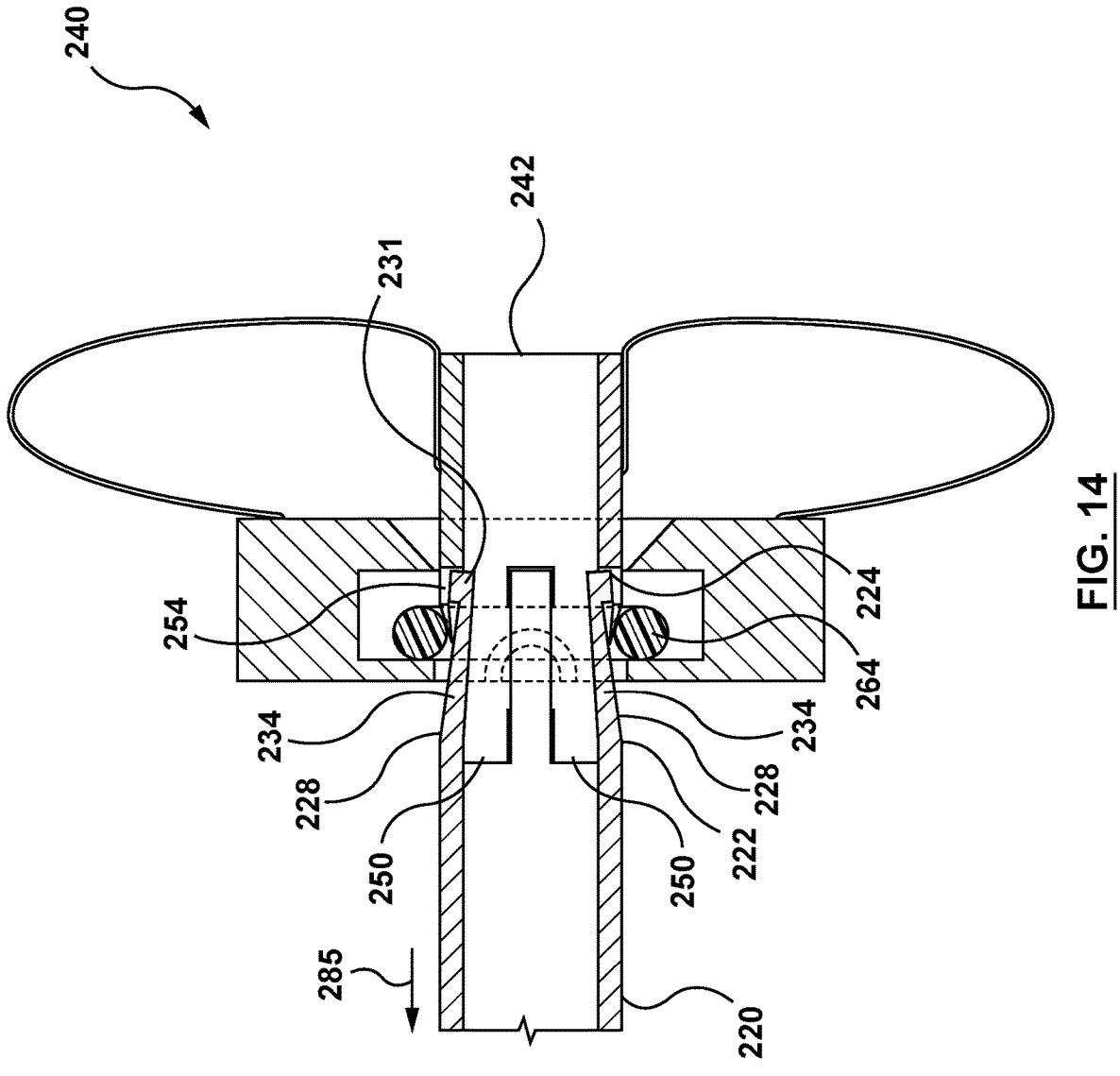
FIG. 14 is a side view illustration of the nosecone and the distal end of the inner shaft of the delivery system of FIG. 2, wherein the inner member of the nosecone is releasing from the distal end of the inner shaft.
Figure 15:
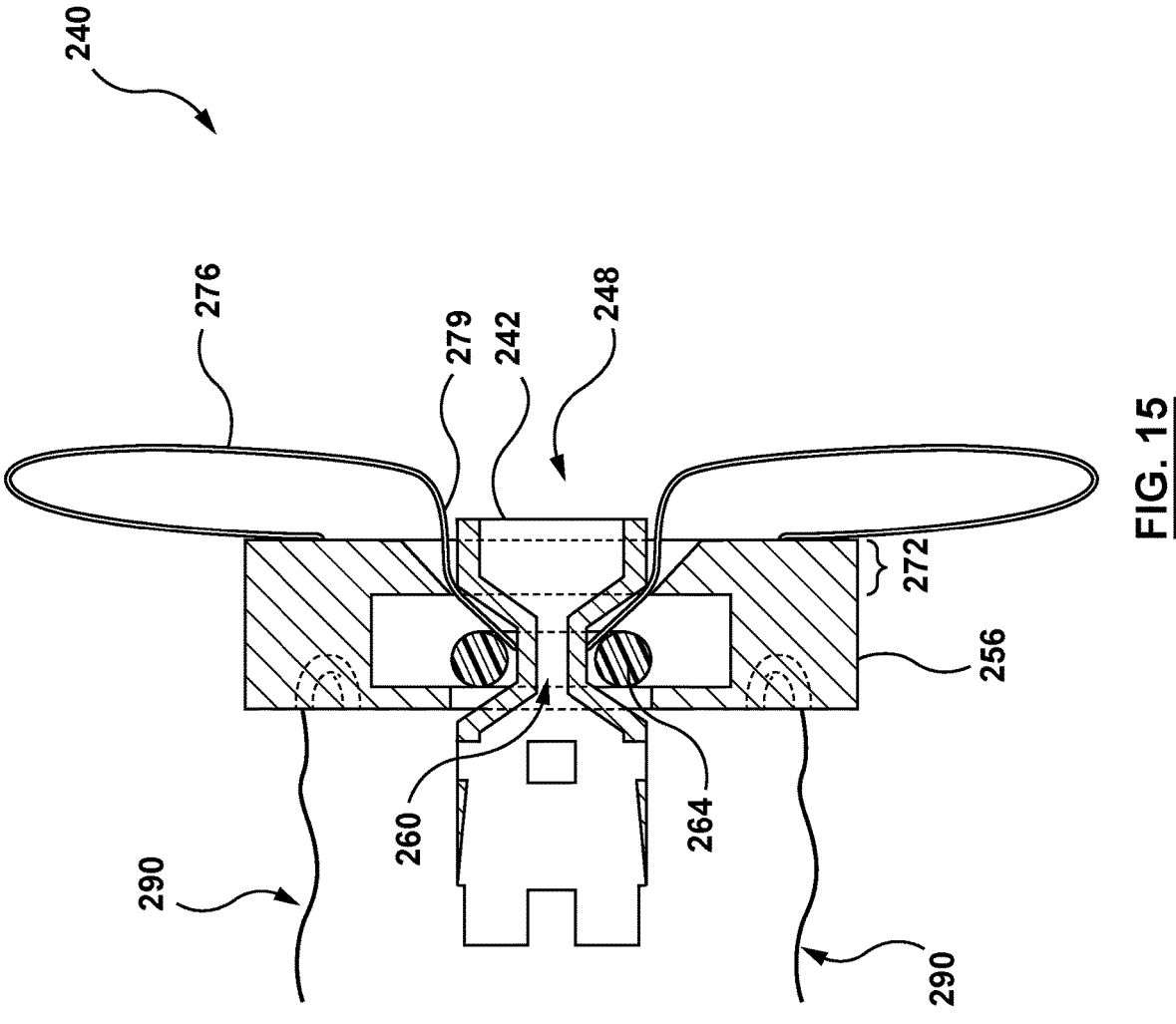
FIG. 15 is a side view illustration of the nosecone and a distal end of an inner shaft of the delivery system of FIG. 2, wherein the inner member of the nosecone is released from the distal end of the inner shaft such that the nosecone and the distal end of the inner shaft are not coupled together.

O-ring 264, shown in FIGS. 11-12, is a ring or annular component defining a lumen 266. O-ring 264 is disposed within cavity 271 of central portion 268 of retainer 256 such that lumen 266 of O-ring 264 aligns with a first longitudinal axis LA1 of retainer 256, as shown in FIG. 12. Stated another way, O-ring 264 is concentrically disposed within retainer 256. O-ring 264 includes a radially collapsed state wherein the distal portion of inner shaft 220 is not received therein and lumen 266 of O-ring 264 has cross-sectional dimension $CD_{ORC}$, as shown in FIG. 12. Cross-sectional dimension $CD_{ORC}$ is smaller than a cross-sectional dimen-sion $CD_{IS}$ of the distal portion of inner shaft 220, as shown in FIG. 13. O-ring 264 further includes a radially expanded state, as shown in FIG. 13, wherein the distal portion of inner shaft 220 is received within and radially expands lumen 266 of O-ring 264 such that lumen 266 has a cross-sectional dimension $CD_{ORE}$. Thus, cross-sectional dimension $CD_{ORE}$ of O-ring 264 is larger than cross-sectional dimension $CD_{IS}$ of the distal portion of inner shaft 220. O-ring 264 is configured such that O-ring 264 transitions from the radially collapsed state to the radially expanded state as inner shaft 220 is received therethrough. In other words, lumen 266 expands to receive inner shaft 220. When so disposed, the elastic properties and associated inward radial force of expanded O-ring 264 frictionally retains inner shaft 220 therein. O-ring 264 is further configured to receive a distal portion of inner shaft 220 and a portion of inner member 242 as the delivery device 202 is retracted therethrough, as shown in FIGS. 13-15. O-ring 264 is yet further configured to collapse inner member 242 when received therein such that nosecone 240 is uncoupled from inner shaft 220, as shown in FIGS. 13-15 and described in greater detail below. Thus, the inward radial force of O-ring 264 in the radially collapsed state is greater than the spring force of inner member 242. O-ring 264 is constructed of a shape memory material with a pre-set shape in the radially collapsed state. O-ring 264 may be formed of a semi-compressible elastic material for example, and not by way of limitation, of nitrile (NBR), tetrafluoroethylene/propylene (TFE/P), ethylene propylene diene terpolymer (EPDM), or other metals/elastomers/composite having elastic properties to permit expansion and recoil suitable for the purposes described herein.

Figure 5:
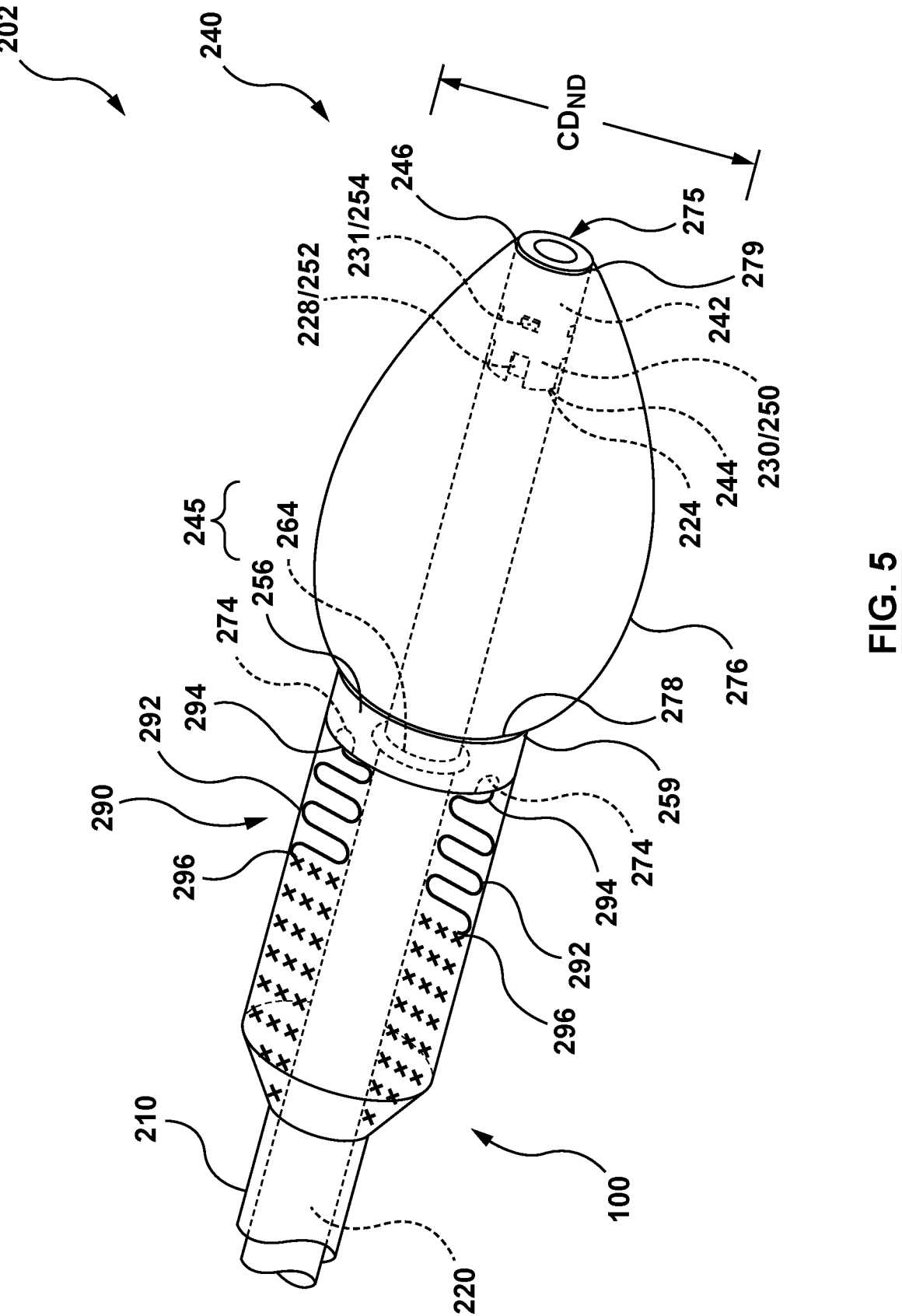
FIG. 5 is a perspective illustration of the distal portion of the delivery system of FIG. 2, wherein the nosecone is in its delivery configuration.

In an embodiment, each tether channel 274 of retainer 256 is a generally u-shaped channel, as shown in FIG. 11. Each tether channel 274 is configured to receive a tether 292 (not shown in FIG. 11) therethrough. Each tether channel 274 is further configured to couple a first end 294 (not shown in FIG. 11) of each corresponding tether 292 to retainer 256, as shown in FIG. 5 and as described in greater detail below. Each tether channel 274 is defined by retainer 256 and begins and ends at proximal end 258 of retainer 256, extending distally as shown in FIG. 11. While FIGS. 11-12 show two (2) tether channels 274, this is not meant to limit the design, and more or fewer tether channels 274 may be utilized. Each tether 292, shown in FIG. 5, may be coupled to a corresponding tether channel 274 for example, and not by way of limitation, by adhesives, fusing, welding, tying, or other methods suitable for the purposes described herein.

Figure 6:
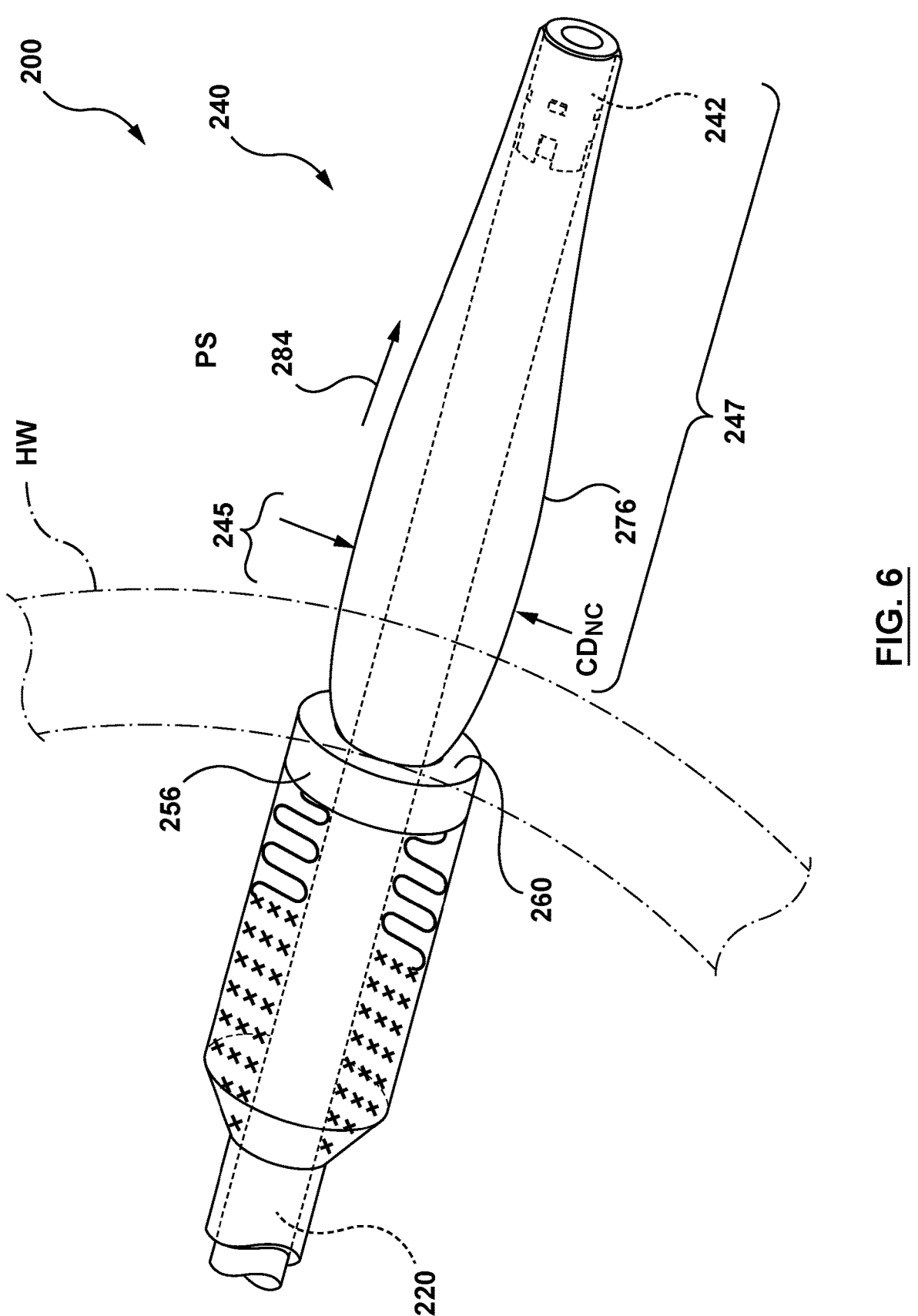
FIG. 6 is a perspective illustration of the distal portion of the delivery system of FIG. 2, wherein the nosecone is in its radially compressed configuration.
Figure 7:
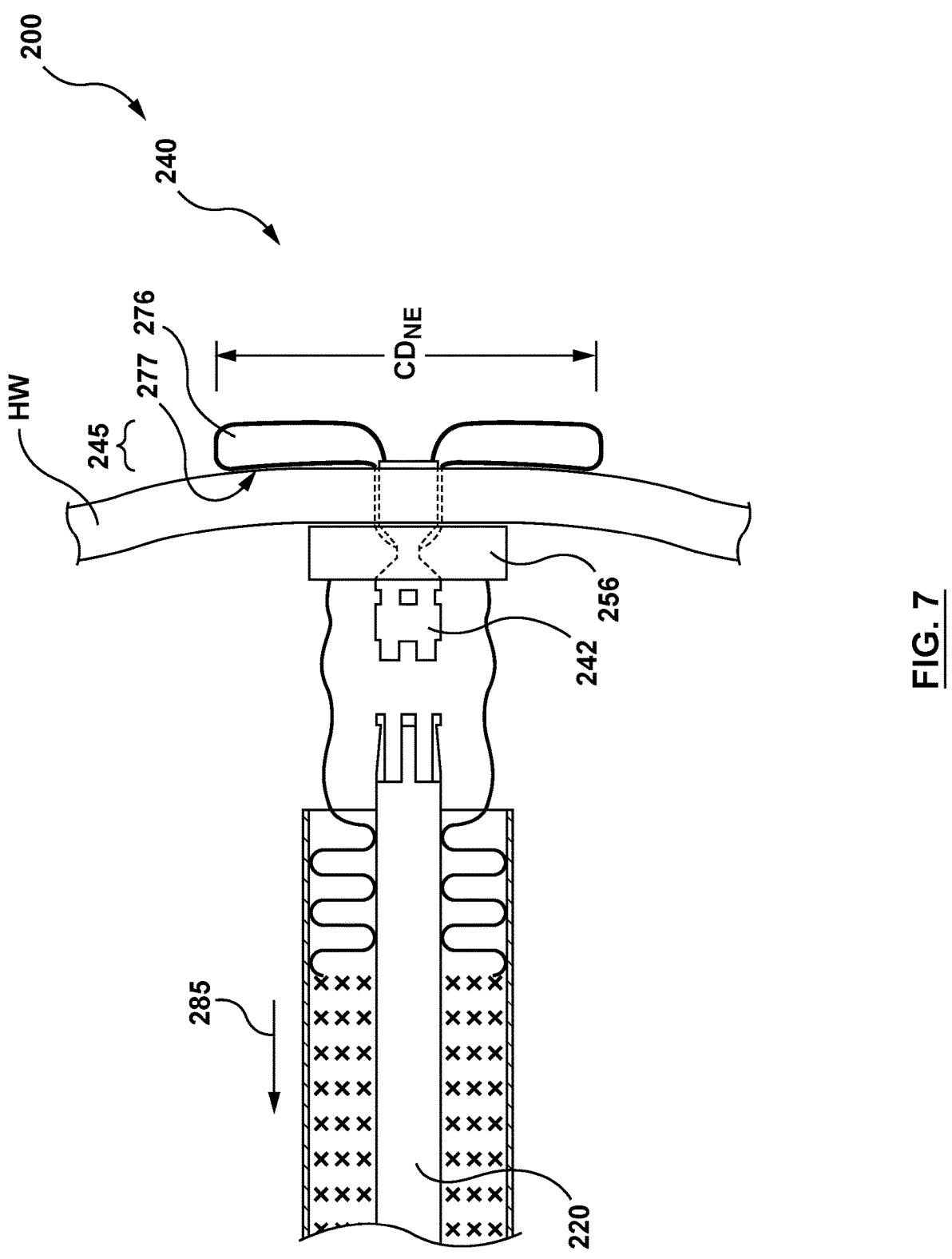
FIG. 7 is a side view illustration of the distal portion of the delivery system of FIG. 2, wherein the nosecone is in its radially expanded configuration.

Referring back to FIG. 5, nosecone plug 276 of nosecone 240 is a semi-flexible component having a general conical shape including a proximal end 278 and a distal end 279. Nosecone plug 276 defines a lumen 275 therethrough configured to receive a portion of inner shaft 220 and/or a portion of inner member 242 therein. Proximal end 278 is coupled to distal end 259 of retainer 256. Distal end 279 of nosecone plug 276 is coupled to distal end 246 of inner member 242. Nosecone plug 276 of nosecone 240 is configured to deform as inner member 242 is moved relative to retainer 256, such that nosecone 240 may transition from the delivery configuration of FIG. 5 to the radially collapsed configuration of FIG. 6, and further to the radially expanded configuration of FIG. 7. Accordingly, when nosecone 240 is in the delivery configuration of FIG. 5, nosecone plug 276 has the general conical shape for delivery to a desired treatment location. When nosecone 240 is in the radially collapsed configuration with inner member 242 advance distally and spaced axially from retainer 256 to traverse through a heart wall, nosecone plug 276 stretches axially as shown in FIG. 6. Further, when nosecone 240 is in the radially expanded configuration, with inner member 242 received within retainer 256, nosecone plug 276 expands radially as shown in FIG. 7 wherein outer surface 277 of nosecone plug 276 is in contact with the outer surface of heart wall HW, as described in greater detail below. Thus, nosecone plug 276 is configured to deform (i.e., stretch axially and expand radially) such that nosecone 240 may transition from the delivery configuration to the radially compressed configuration to transit the heart wall and to the radially expanded configuration such that nosecone 240 anchors stented prosthetic heart valve 100 from an outer wall of the heart, as will be described in greater detail below. Nosecone plug 276 is further configured to seal the transit point, or piercing in the heart wall HW through which a portion of nosecone 240 has traversed. Nosecone plug 276 is a semi-rigid or semi-flexible elastic member and may be constructed of braided or woven materials such as, but not limited to Nitinol, stainless steel, nylon, polybutester, polypropylene, silk, polyester, or other materials suitable for the purposes described herein. Nosecone plug 276 may be coupled to retainer 256 and inner member 242 for example, and not by way of limitation, by adhesives, fusing, welding, tying, or other methods suitable for the purposes described herein.

With nosecone 240 fully described, tether component 290 will now be described with reference to FIGS. 5-7. Tether component 290 includes a plurality of tethers 292. Tether component 290 is configured to couple retainer 256 of nosecone 240 to stented prosthetic heart valve 100. Accordingly, each tether 292 of tether component 290 includes first end 294 coupled to corresponding tether channel 274 of retainer 256, and a second end 296 coupled to stented prosthetic heart valve 100. Stated another way, each first end 294 is coupled to nosecone 240 and each second end 296 is coupled to stented prosthetic heart valve 100. Tether component 290 is disposed within outer sheath 210 of delivery device 202 during delivery of stented prosthetic heart valve 100 to the desired treatment location. Tether component 290 is released from outer sheath 210 by retraction of outer sheath 210 as part of the final positioning and anchoring of stented prosthetic heart valve 100. More specifically, when released from outer sheath 210, tether component 290 is of a length that provides proper locational placement of stented prosthetic heart valve 100 at the desired deployment site, as described in greater detail below. The embodiment of FIGS. 5-7 shows two (2) tethers 292, however it is understood that more or fewer tethers 292 may be provided depending on the specific requirements of the components, devices, and procedures being utilized. Each tether 292 is an elongate member such as a wire or suture, and may be constructed of materials such as, but not limited to stainless steel, Nitinol, nylon, polybutester, polypropylene, silk, polyester, or other materials suitable for the purposes described herein. Each tether 292 may be connected to corresponding tether channel 274 of retainer 256 and stented prosthetic heart valve 100 by methods such as, but not limited to adhesives, fusing, welding, sutures, or otherwise tied.

With an understanding of the components of delivery system 200 above, it is now possible to describe the interactions of the various components to deliver, position, deploy, and anchor stented prosthetic heart valve 100 at the site of a native valve. Delivery system 200, with stented prosthetic heart valve 100 in the radially collapsed configuration disposed therein, is assembled as shown in FIG. 5. Inner shaft 220 is disposed within O-ring 264, wherein O-ring 264 is in the radially expanded state. O-ring 264 is disposed proximal of legs 228 of inner shaft 220 and distal member 242. Distal end 224 of inner shaft 220 abuts and is coupled to proximal end 244 of inner member 242 such that each leg 228 of inner shaft 220 is disposed within each corresponding gap 252 of inner member 242. Further, each leg 250 of inner member 242 is disposed within each corresponding gap 230 of inner shaft 220. Even further, each tab 231 of each leg 228 is disposed within the corresponding slot 254 of inner member 242 such that nosecone 240 is removably coupled to distal end 224 of inner shaft 220. As shown in FIG. 14, nosecone plug 276 has the general conical shape for delivery to a desired treatment location. First end 294 of each tether 292 of tether component 290 is coupled to each corresponding tether channel 274 of retainer 256 and second end 296 of each tether 292 is coupled to stented prosthetic heart valve 100.

With the components of delivery system 200 so assembled and configured, delivery system 200 is advanced to a desired deployment site of a native valve, such as a mitral valve. Delivery system 200 is advanced such that nosecone 240 is disposed adjacent to an interior surface of a wall HW of the heart, at or adjacent to the apex of the left ventricle. Inner shaft 220 is advanced distally relative to retainer 256, in the direction of arrow 284 of FIG. 6, axially stretching nosecone plug 276 such that nosecone 240 transitions from the delivery configuration of FIG. 5 to the radially compressed configuration shown in FIG. 6. Once nosecone 240 is in the radially compressed configuration and the wall HW of the heart has been punctured by a needle tube or other suitable device, delivery system 200 may be advanced distally such that proximal portion 245 of nosecone 240 in the radially collapsed configuration transits the wall HW of the heart, as shown in FIG. 6. Delivery system 200 is advanced until proximal portion 245 of nosecone 240 is disposed in the pericardial space PS outside the heart and retainer 256 is disposed with distal end 260 abutting the interior surface of the wall HW of the heart.

Once proximal portion 245 of nosecone 240 is disposed in the pericardial space PS, inner shaft 220 and removably coupled inner member 242 of nosecone 240 may be retracted proximally in a direction of arrow 285, shown in FIG. 7. Inner shaft 220 and inner member 242 are retracted proximally such the proximal portion of nosecone plug 276 outside the heart wall HW inverts, or mushrooms upon itself, transitioning the nosecone 240 from the radially collapsed configuration of FIG. 6 to the radially expanded configuration of FIG. 7. Inversion of nosecone plug 276 and subsequent release of nosecone 240 from inner shaft 220 is shown in greater detail in FIGS. 13-15. Distal portion 272 of retainer 256 guides inner shaft 220 through lumen 260 of retainer 256, as shown in FIG. 13. Inner shaft 220 is further retracted proximally in the direction of arrow 285 such that legs 228 of inner shaft 220 and corresponding legs 250 of inner member 242 move proximally through O-ring 264, as shown in FIG. 14. As each tapered portion 234 of each leg 228 moves proximally through O-ring 264, the elastic characteristic of O-ring 264, or the desire of O-ring 264 to recoil to the radially collapsed state, exerts an inward radial force against each tapered portion 234 of each leg 228 and an outer surface of inner member 242 of nosecone 240. Each tapered portion 234 of each leg 228 is configured such that each tapered portion 234 provides less outward radial spring force at distal end 224 than at proximal end 222. As described previously, inner member 242 is configured with an outward radial spring force weaker than the inward radial force of O-ring 264. Thus, as inner shaft 220 is retracted further proximally through O-ring 264, the outward radial spring force of each leg 228 weakens distally along the length of each tapered portion 234 until the inward radial force of O-ring 264 overpowers the outward radial spring force of each tapered portion 234 and the outward radial spring force of inner member 242 such that each leg 228 and inner member 242 compresses radially inward. Radial compression of each leg 228 radially compresses each corresponding tab 231 disposed within each corresponding slot 254 of inner member 242. Continued retraction proximally of inner shaft 220 continues compression of inner member 242 of nosecone 240 and compression of each leg 228 of inner shaft 220 until each tab 231 no longer engages each corresponding slot 254 of inner member 242 of nosecone 240. When each tab 231 of inner shaft 220 is no longer engaged within the corresponding slot 254 of nosecone 240, inner shaft 220 releases from nosecone 240. Inner member 242 in thus transitioned from the radially expanded state to the radially collapsed state and is retained within O-ring 264 by frictional forces (pre-set memory recoil) of O-ring 264 radially inward against an outer surface of inner member 242, as shown in FIG. 15. Since inner member 242 of nosecone 240 is less stiff than O-ring 264, a portion of inner member 242 proximal to O-ring 264 expands more radially than O-ring 264, increasing the retention force. Nosecone 240 is now coupled to delivery system 200 only by untensioned tether component 290. Moreover, as inner member 242 is retracted within lumen 260 of retainer 256 and is collapsed inward by O-ring 264, the funnel shape of distal portion 272 of retainer 256 assists the collapse of distal end 279 of nosecone plug 276 radially inward such that nosecone plug 276 plugs lumen 248 of inner member 242.

While the embodiment described herein and in FIGS. 2-15 include an O-ring configured to release nosecone 240 from inner shaft 220, this is not meant to limit the design, and other configurations to release nosecone 240 from inner shaft 220 may be utilized, such as, but not limited to helical threads, rotational detents, or any other selective release mechanisms suitable for the purposes described herein.

Delivery system 200 is retracted proximally until tether component 290 becomes taut. Tautness of tether component 290 correctly positions stented prosthetic heart valve 100 within an annulus of the native valve. Outer sheath 210 is retracted such that stented prosthetic heart valve 100 is released and expands to the radially expanded configuration, engaging an interior wall of the native valve. Thus, nosecone 240 and coupled tether component 290 provides both proper positioning and anchoring of stented prosthetic heart valve 100 within the native valve. Stated another way, nosecone 240 in the radially expanded configuration properly locates stented prosthetic heart valve 100 within the native valve and further anchors stented prosthetic heart valve 100 to prevent migration from the desired deployment site.

Figure 16:
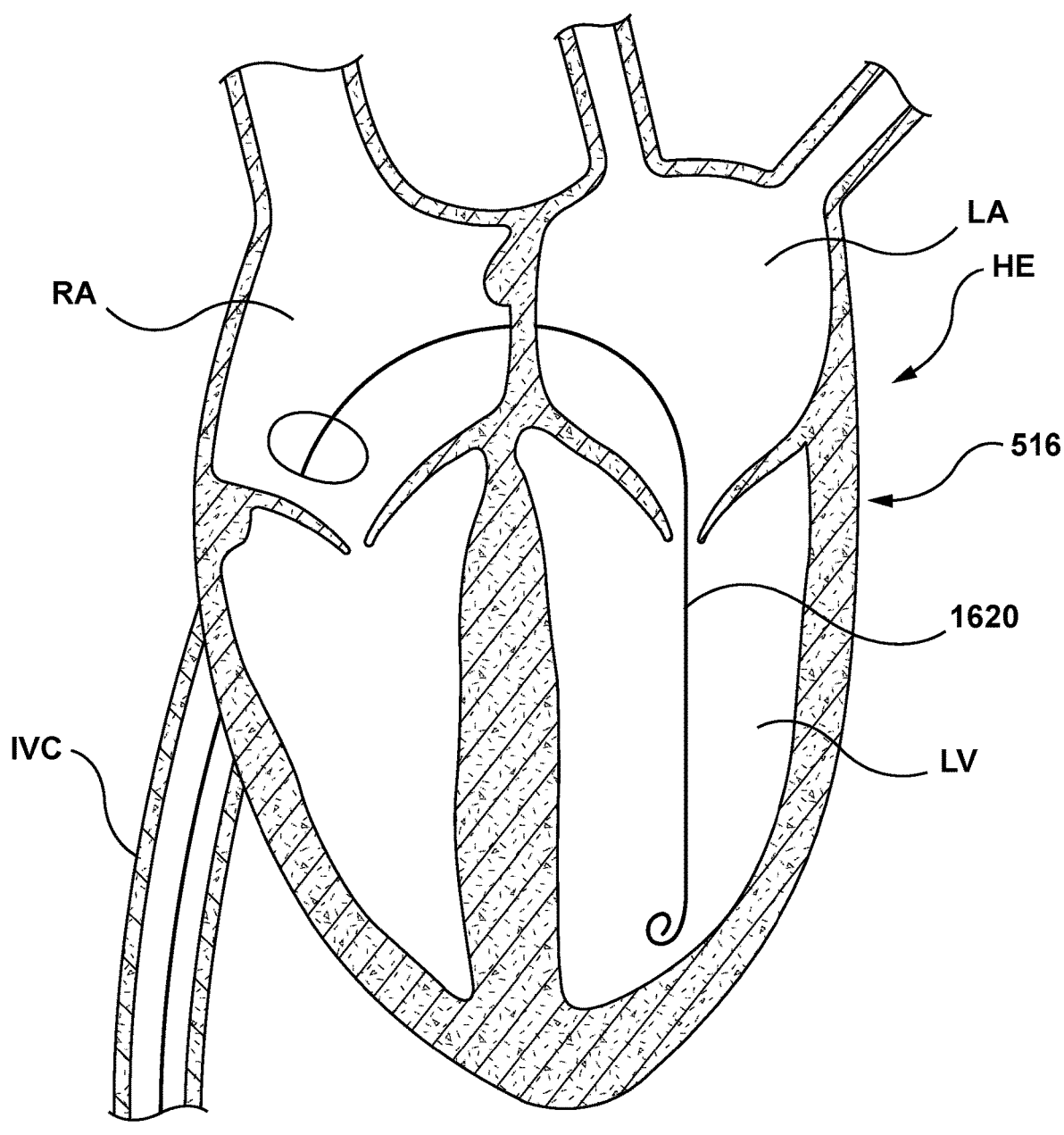
FIG. 16 is a sectional cut-away illustration of the heart illustrating a method step of using the delivery system of FIG. 2 to deliver and position a mitral valve prosthesis within a native mitral valve using a trans-septal approach in accordance with an embodiment hereof, wherein a guidewire is shown being advanced into the left ventricle of the heart.

FIGS. 16-25 show schematically an embodiment of a method of replacing a mitral valve with delivery system 200 of the present disclosure. Using established percutaneous transcatheter procedures, a guidewire 1620 is advanced distally through the vasculature of a patient and into a left ventricle LV of a heart HE, as shown in FIG. 16. While the method shown in FIG. 16 shows guidewire 1620 accessing left ventricle LV by advancement through the inferior vena cava IVC into the right atrium RA and then into the left atrium LA via trans-septal puncture, this is not meant to limit the method and those skilled in the art would recognize that other paths may be utilized.

Figure 17:
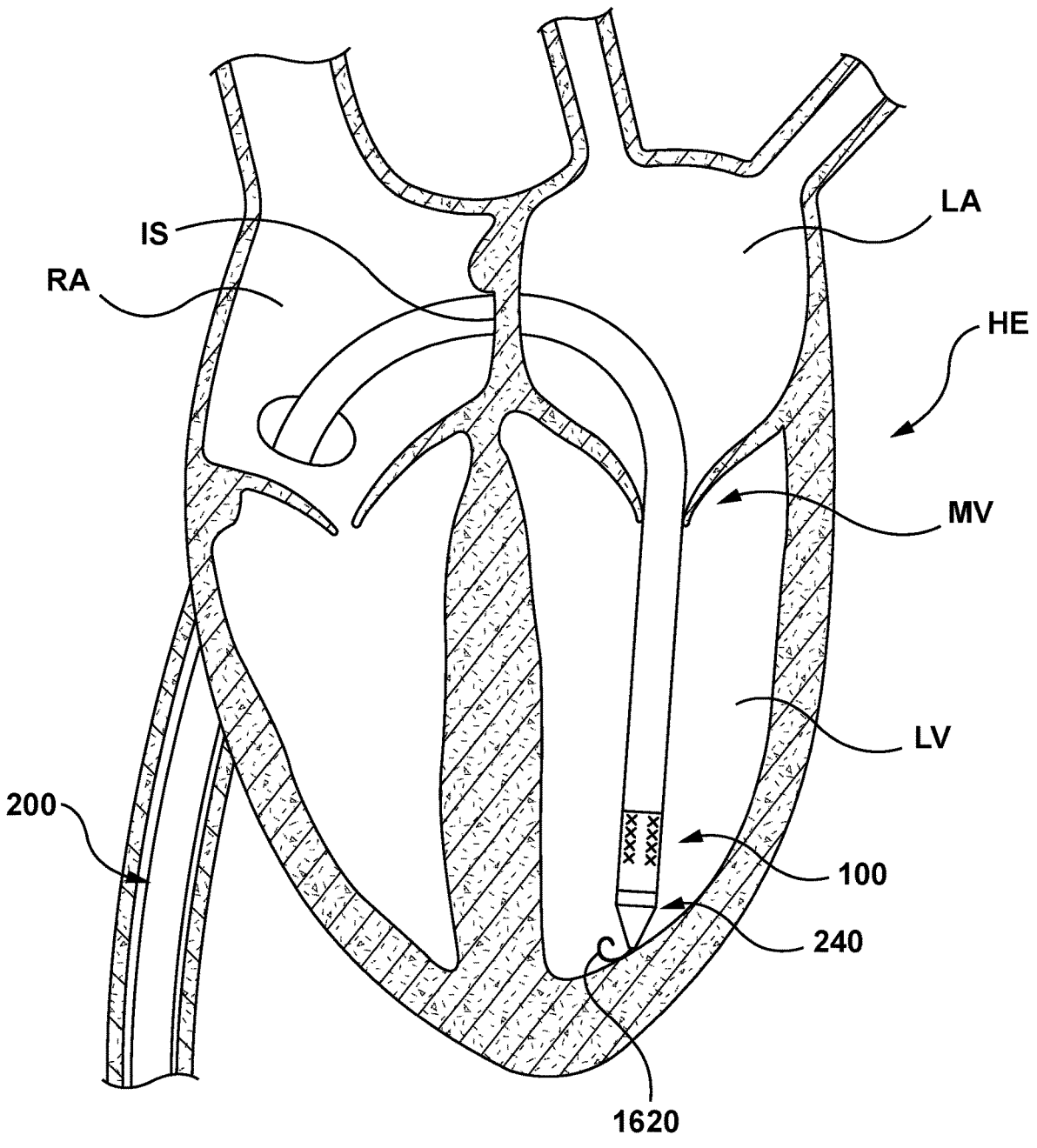
FIG. 17 is a sectional cut-away illustration of the heart illustrating a method step of using the delivery system of FIG. 2 to deliver and position a mitral valve prosthesis within a native mitral valve using a trans-septal approach, wherein the delivery system of FIG. 2 is advanced over the guidewire and the nosecone is positioned against an interior wall at or adjacent to an apex of the left ventricle.

With guidewire 1620 so disposed, a clinician advances delivery system 200, with nosecone 240 in the delivery configuration and stented prosthetic heart valve 100 disposed within outer sheath 210 in a radially collapsed configuration, over guidewire 1620, as shown in FIG. 17. Delivery system 200 is advanced over guidewire 1620 into right atrium RA. Next, delivery system 200 is advanced through an interatrial septum IS and into left atrium LA of the heart HE. Once advanced into left atrium LA, delivery system 200 is next advanced through mitral valve MV and into left ventricle LV. The delivery system 200 is advanced until nosecone 240 is disposed adjacent an interior wall (endocardial surface) at or adjacent to an apex of left ventricle LV.

Figure 18:
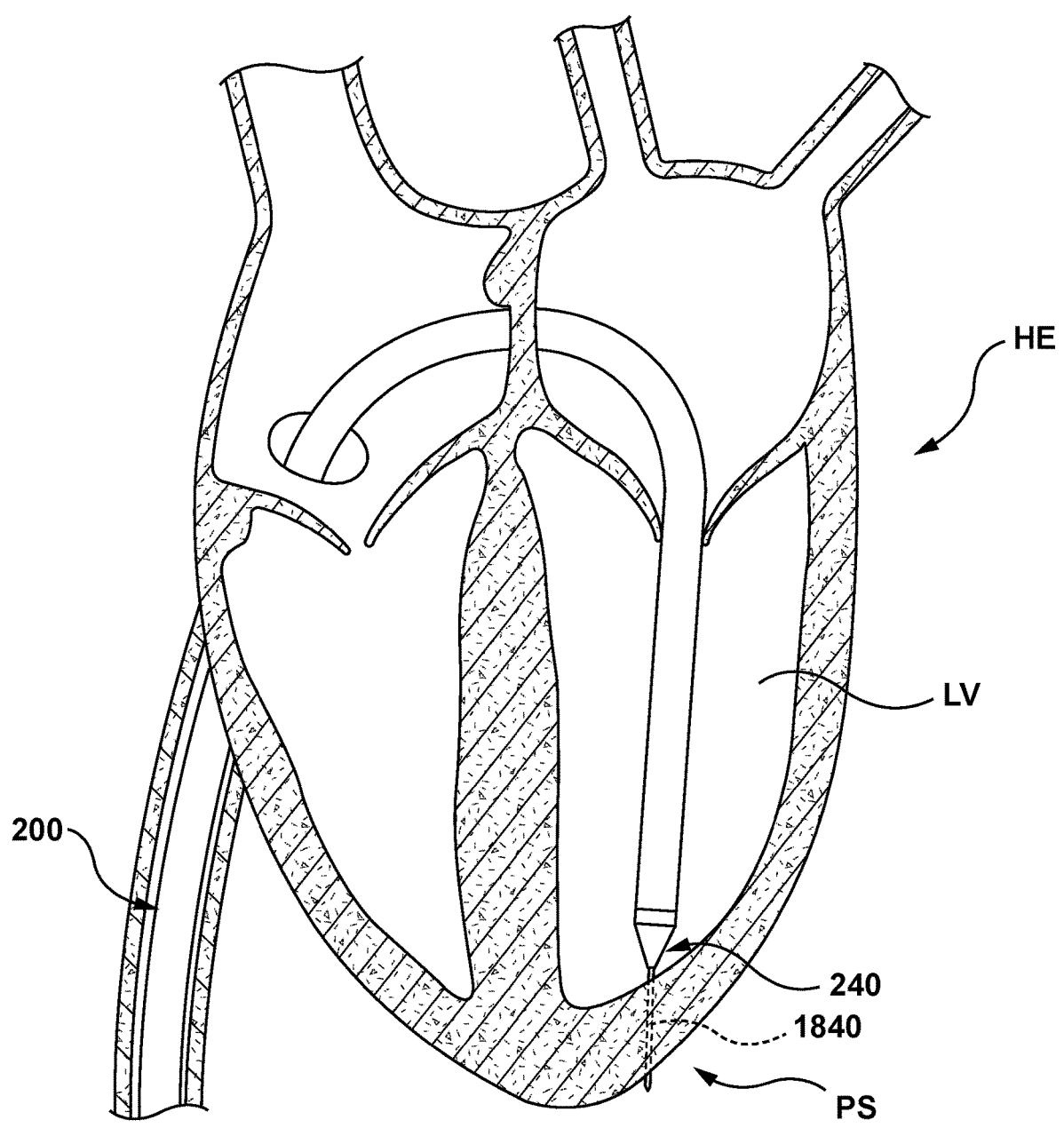
FIG. 18 is a sectional cutaway illustration of the heart illustrating a method step of using the delivery system of FIG. 2 to deliver and position a mitral valve prosthesis within a native mitral valve using a trans-septal approach, wherein a needle tube is advanced through the myocardial wall of the left ventricle.

With nosecone 240 disposed adjacent the interior wall of at the apex of left ventricle LV, as shown in FIG. 18, the clinician retracts guidewire 1620 from delivery system 200 proximally and exchanges guidewire 1620 for a needle tube 1840 using established procedures. Needle tube 1840 is advanced through the wall (myocardium) of left ventricle LV and into pericardial space PS outside heart HE.

Figure 19:
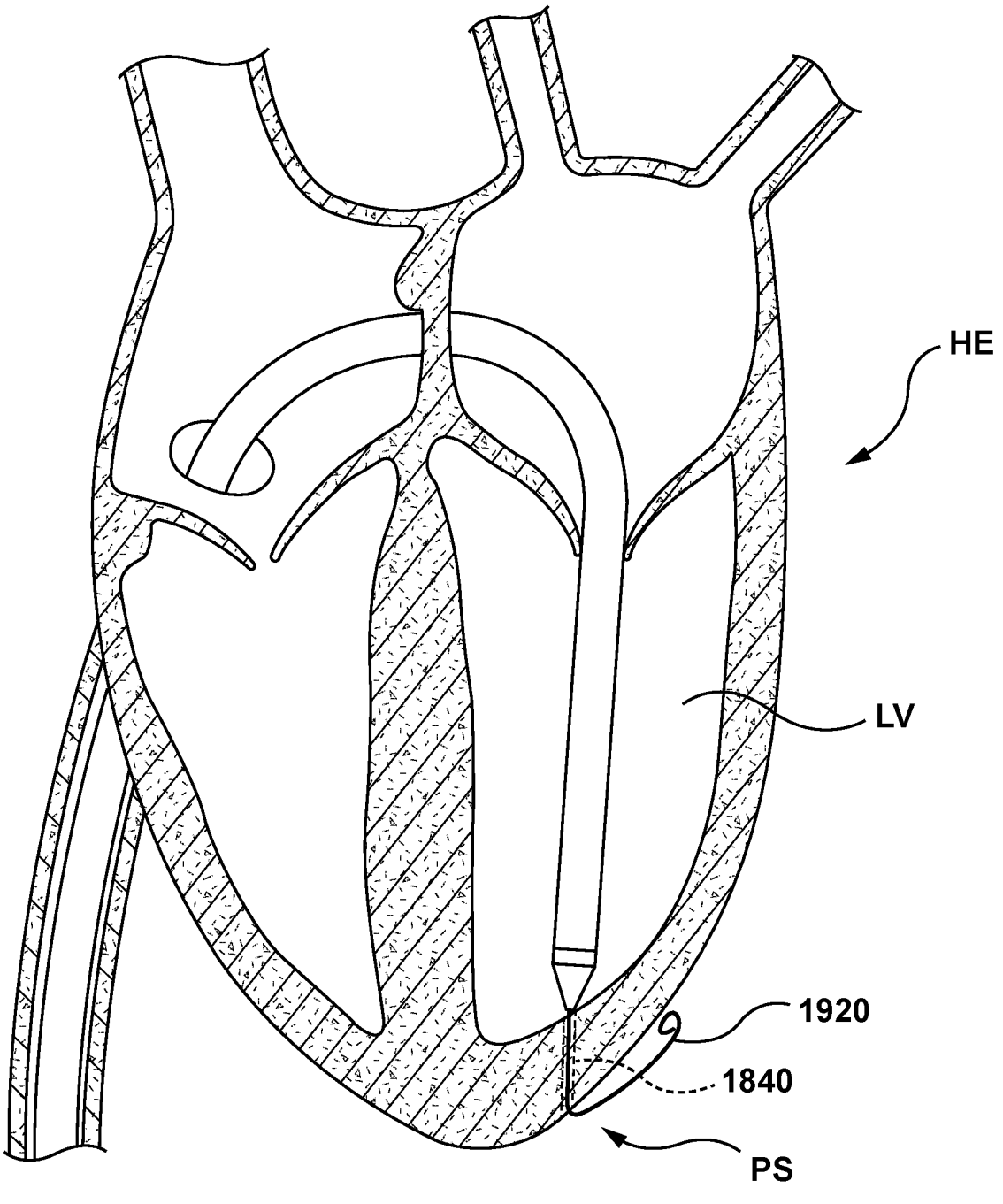
FIG. 19 is a sectional cutaway illustration of the heart illustrating a method step of using the delivery system of FIG. 2 to deliver and position a mitral valve prosthesis within a native mitral valve using a trans-septal approach, wherein a second guidewire is advanced into the pericardial space outside the heart.

With the wall of left ventricle LV so pierced, the clinician advances a second guidewire 1920 through needle tube 1840 and into pericardial space PS, as shown in FIG. 19. Second guidewire 1920 travels along an outer surface of the heart wall of the left ventricle LV of heart HE.

Figure 20:
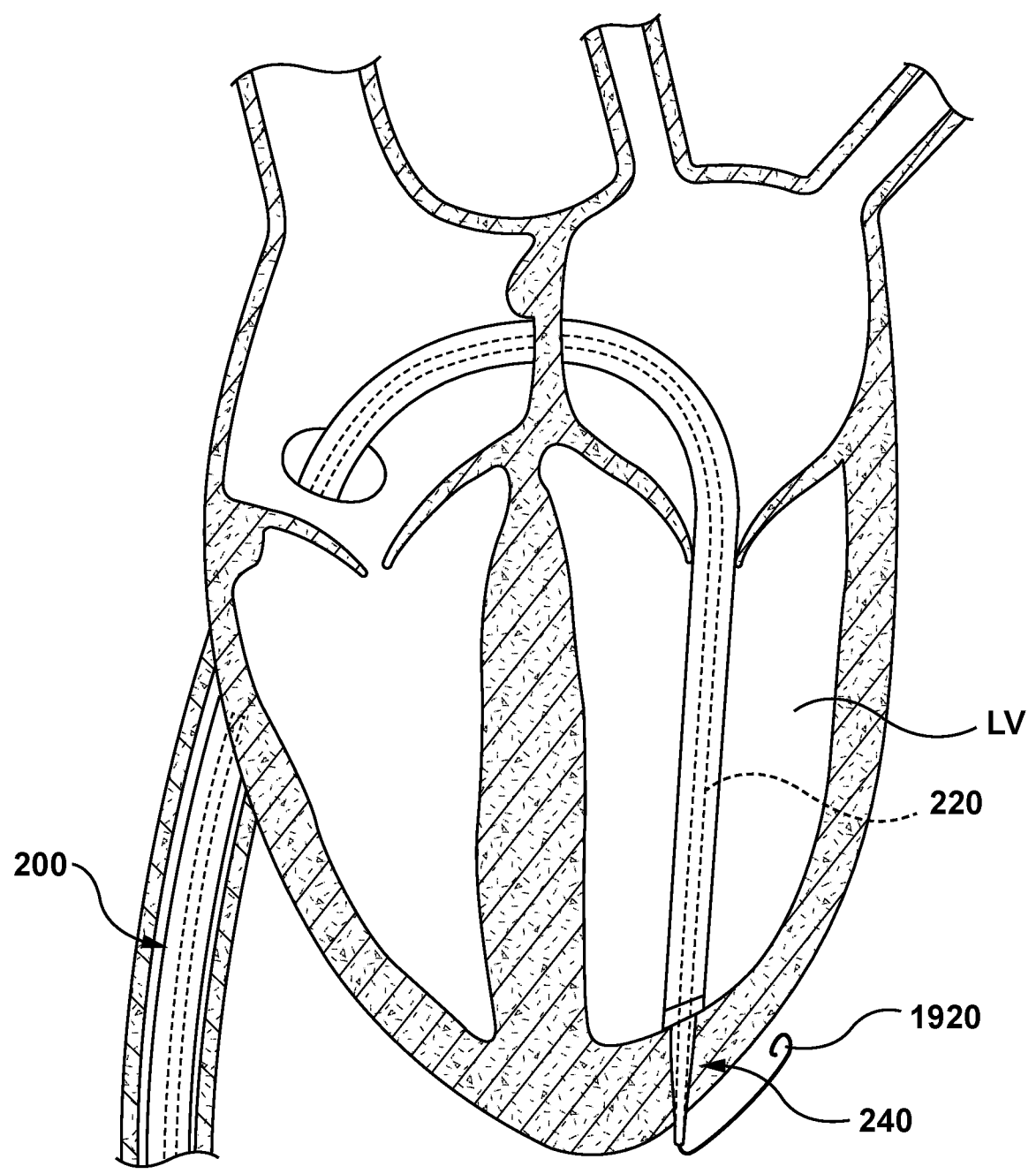
FIG. 20 is a sectional cutaway illustration of the heart illustrating a method step of using the delivery system of FIG. 2 to deliver and position a mitral valve prosthesis within a native mitral valve using a trans-septal approach, wherein the inner shaft is advanced to transition the nosecone to its radially compressed configuration, and the distal portion of the nosecone is advanced through the wall of the left ventricle of the heart.

With second guidewire 1920 so disposed, the clinician advances inner shaft 220 of delivery system 200 such that nosecone 240 transitions from the delivery configuration to the radially compressed configuration. Delivery system 200 is advanced such that a portion of nosecone 240 transits the wall of left ventricle LV, as shown in FIG. 20.

Figure 21:
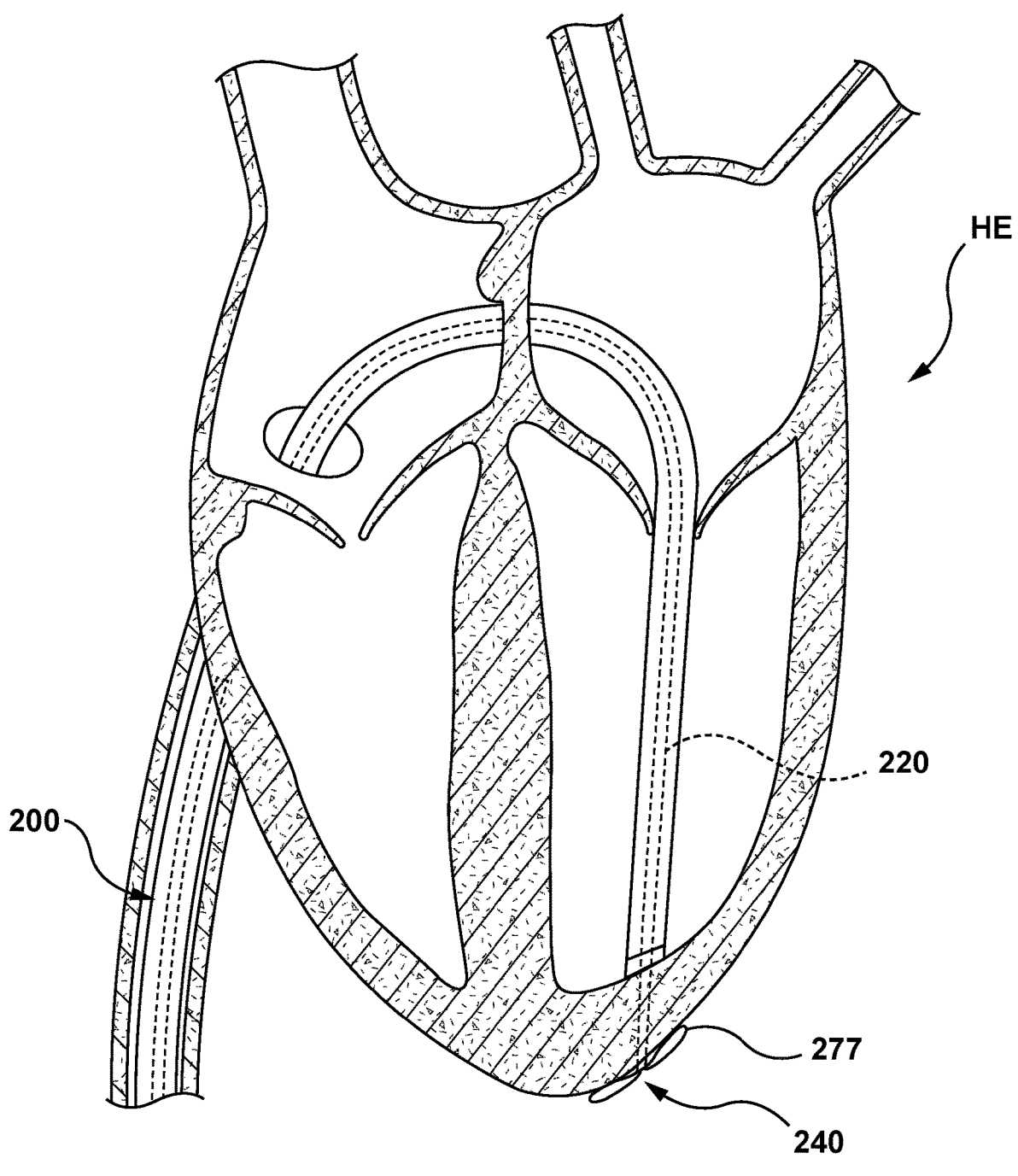
FIG. 21 is a sectional cutaway illustration of the heart illustrating a method step of using the delivery system of FIG. 2 to deliver and position a mitral valve prosthesis within a native mitral valve using a trans-septal approach, wherein the inner shaft is retracted to transition the nosecone to its radially expanded configuration with the outer surface of the nosecone in contact with an outer surface of the heart.

The clinician next retracts second guidewire 1920 proximally. Following retraction of second guidewire 1920, the clinician retracts inner shaft 220 of delivery system 200 such that nosecone 240 mushrooms or inverts and outer surface 277 of nosecone 240 contacts an outer surface of the wall of heart HE. As inner shaft 220 is retracted with the outer surface of nosecone 240 in contact with the outer surface of the heart wall, nosecone 240 transitions from the radially compressed configuration to the radially expanded configuration, as shown in FIG. 21.

Figure 22:
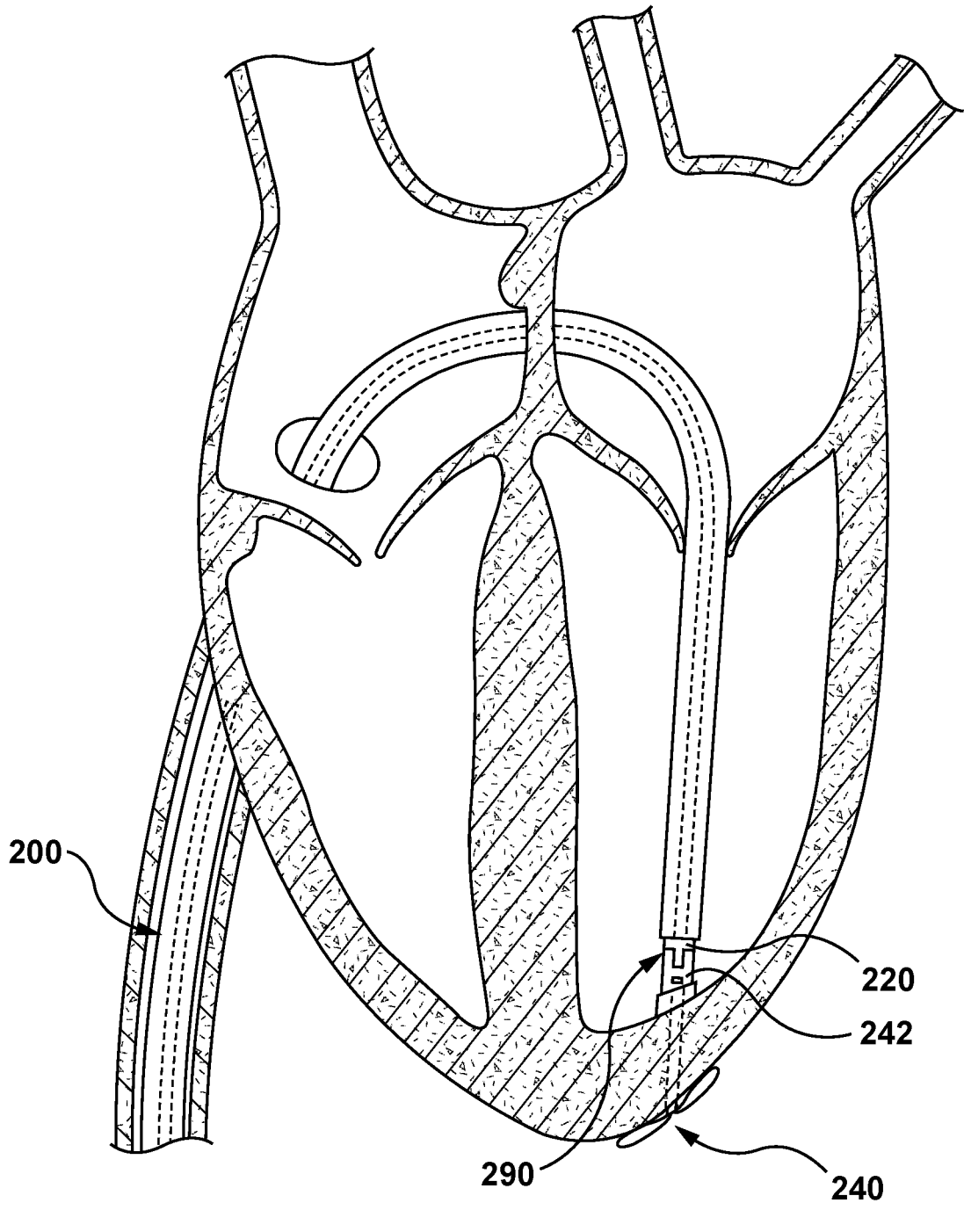
FIG. 22 is a sectional cutaway illustration of the heart illustrating a method step of using the delivery system of FIG. 2 to deliver and position a mitral valve prosthesis within a native mitral valve using a trans-septal approach, wherein the inner shaft is further retracted and the inner shaft releases the nosecone from the delivery system.

With nosecone 240 in the radially expanded configuration, the clinician further retracts inner shaft 220 of delivery system 200 such that inner shaft 220 releases nosecone 240. Nosecone 240 is now coupled to delivery system 200 only by tether component 290. The clinician retracts delivery system 200 proximally, as shown in FIG. 22.

Figure 23:
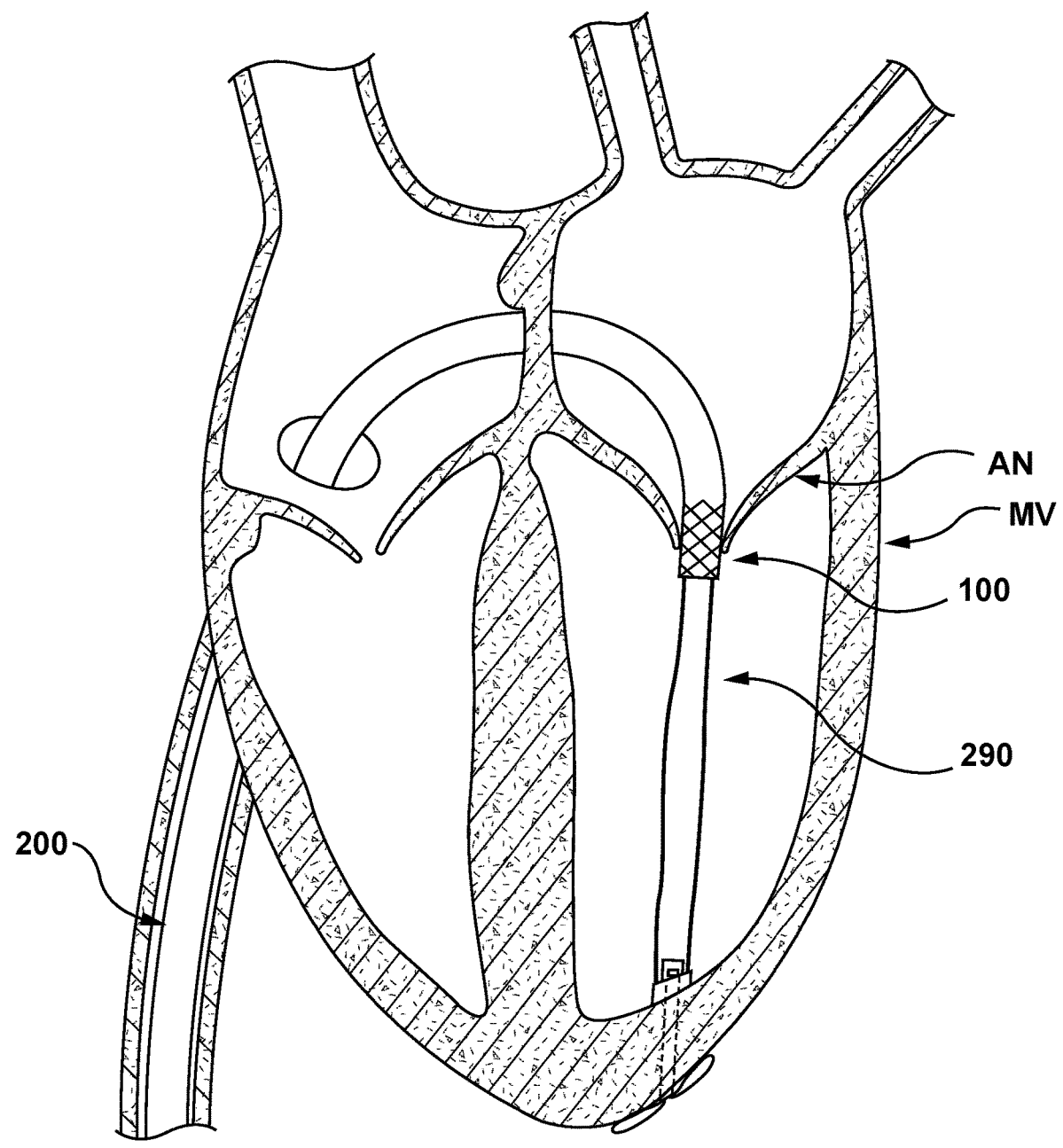
FIG. 23 is a sectional cutaway illustration of the heart illustrating a method step of using the delivery system of FIG. 2 to deliver and position a mitral valve prosthesis within a native mitral valve using a trans-septal approach, wherein the delivery system is retracted until tethers thereof are taut and the mitral valve prosthesis is correctly positioned within the annulus of the native mitral valve.

With nosecone 240 so disposed, the clinician retracts delivery system 200 until tether component 290 is taut. Tautness of tether component 290 correctly positions stented prosthetic heart valve 100 for deployment at the desired deployment site within annulus AN of mitral valve MV, as shown in FIG. 23.

Figure 24:
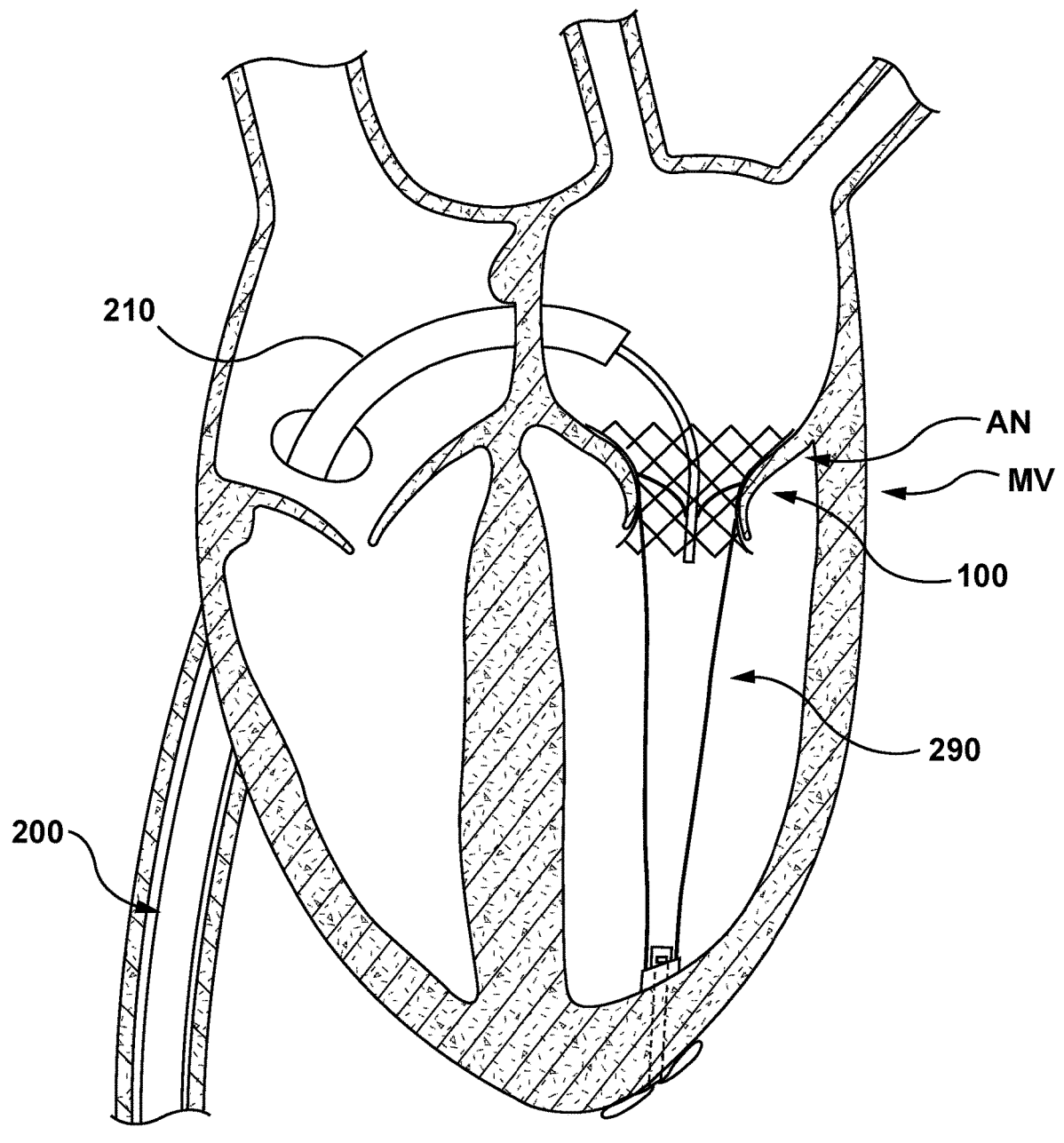
FIG. 24 is a sectional cutaway illustration of the heart illustrating a method step of using the delivery system of FIG. 2 to deliver and position a mitral valve prosthesis within a native mitral valve using a trans-septal approach, wherein the outer sheath of the delivery device is retracted, releasing the mitral valve prosthesis such that the mitral valve prosthesis expands to its radially expanded configuration within the annulus of the native mitral valve.

With stented prosthetic heart valve 100 properly positioned by tautness of tether component 290, the clinician retracts outer sheath 210 of delivery system 200 proximally, thereby releasing stented prosthetic heart valve 100 disposed therein. Stented prosthetic heart valve 100 expands radially to the radially expanded configuration at the desired deployment site. Upon expansion thereof, stented prosthetic heart valve 100 engages an interior wall of annulus AN of mitral valve MV, as shown in FIG. 24.

Figure 25:
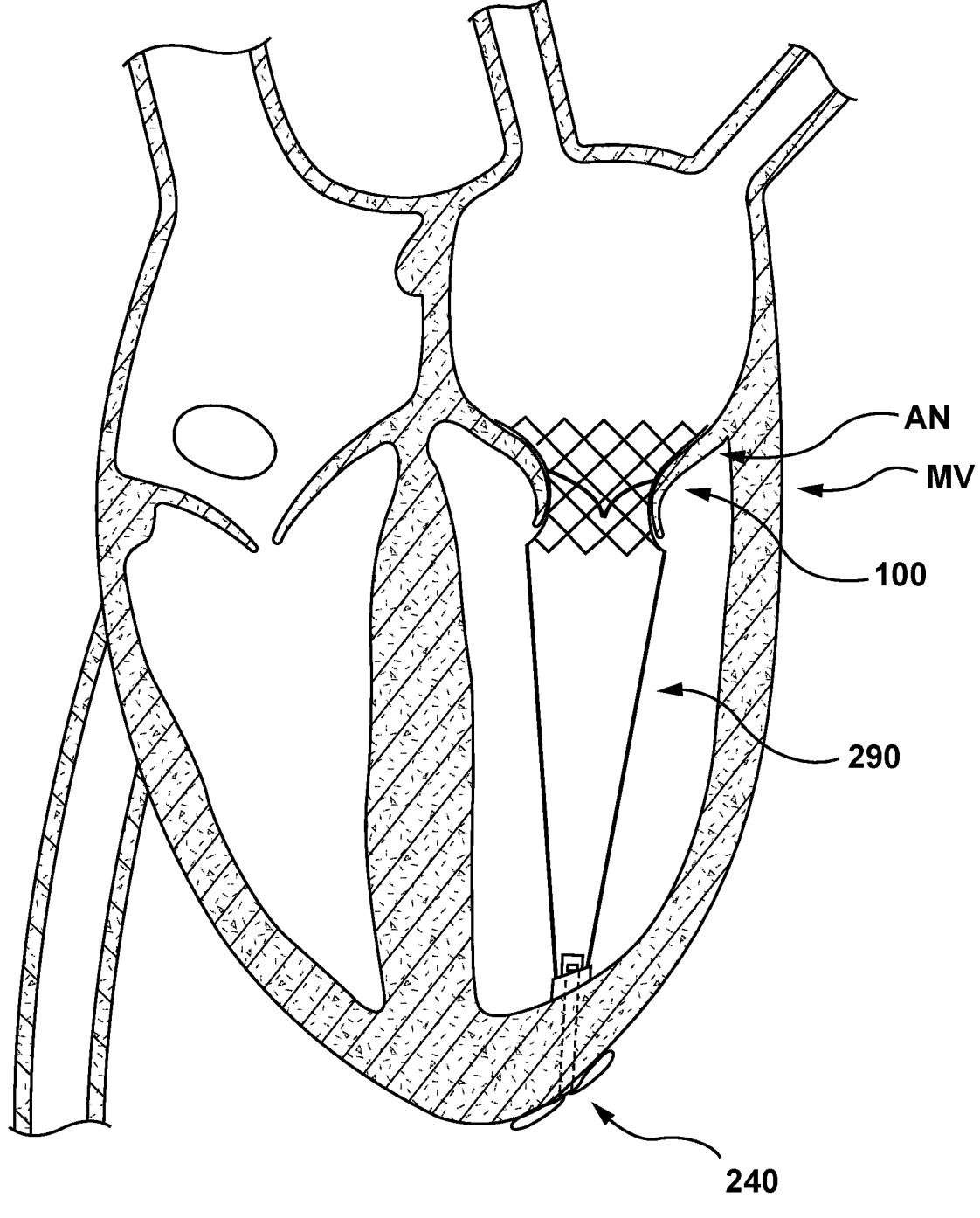
FIG. 25 is a sectional cutaway illustration of the heart illustrating a method step of using the delivery system of FIG. 2 to deliver and position a mitral valve prosthesis within a native mitral valve using a trans-septal approach, wherein the delivery system is retracted leaving the mitral valve prosthesis disposed within the annulus of the native mitral valve and anchored thereto by the nosecone in its radially expanded configuration.

With stented prosthetic heart valve 100 properly deployed, delivery system 200 may be retracted and removed from the patient's vasculature using established procedures. Stented prosthetic heart valve 100 remains in the radially expanded configuration anchored within annulus AN of mitral valve MV, as shown in FIG. 25. Stented prosthetic heart valve 100 is anchored therein by nosecone 240 and taut tether component 290.

While the method of FIGS. 16-25 show an embodiment of stented prosthetic heart valve 100 as a stented prosthetic heart valve deployed within a native mitral valve, those skilled in the art will understand that the method described with FIGS. 16-25 would also apply to other embodiments of stented prosthetic heart valve 100 and at other locations.

Figure 26:
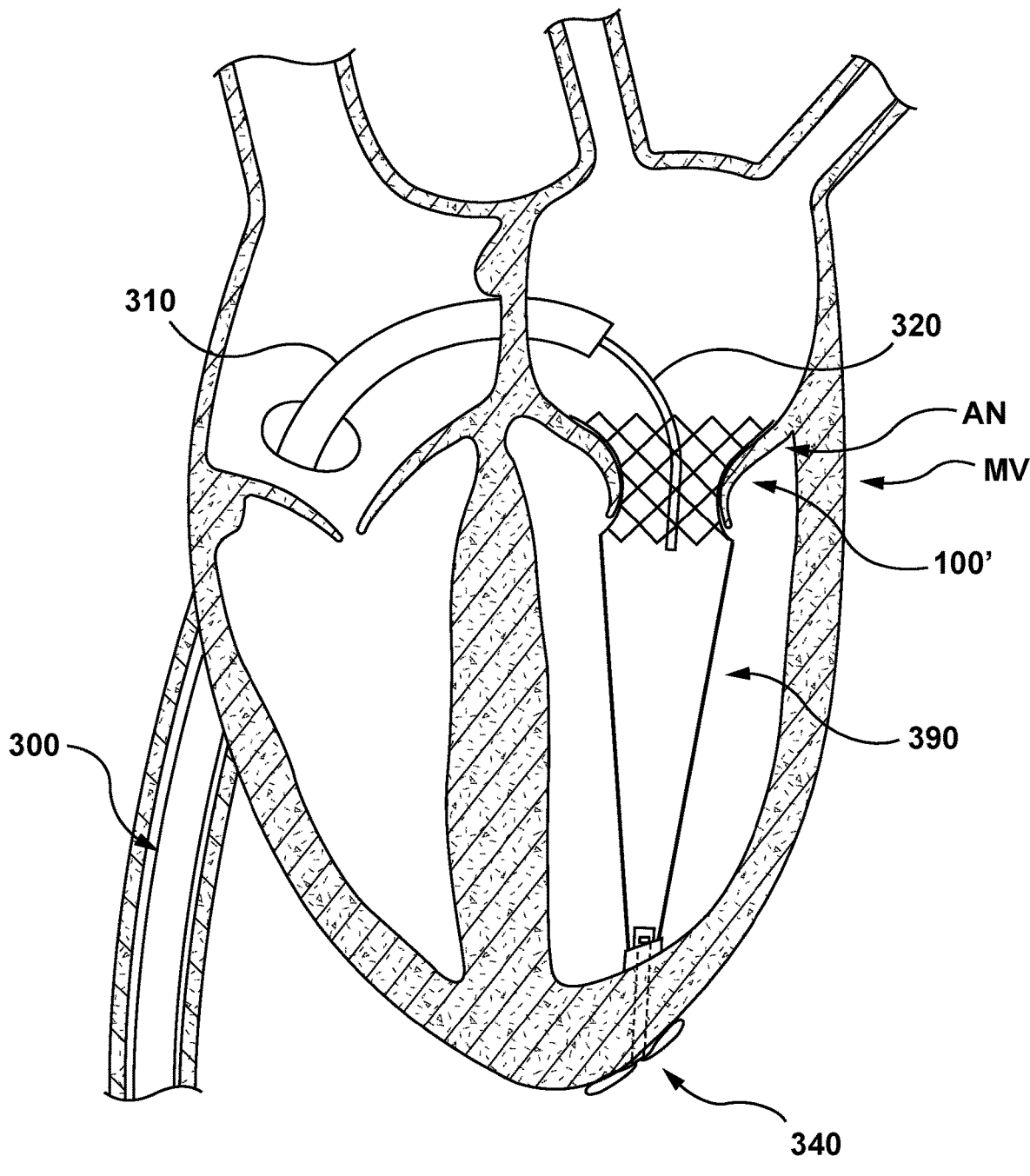
FIG. 26 is a sectional cut-away illustration of the heart illustrating a method step of using a delivery system to deliver and position a mitral valve prosthesis within a native mitral valve using a trans-septal approach in accordance with another embodiment hereof, wherein a docking stent is disposed within the annulus of the native mitral valve and anchored thereto by a nosecone in its radially expanded configuration, with the outer surface of the nosecone in contact with an outer surface of the heart.
Figure 27:
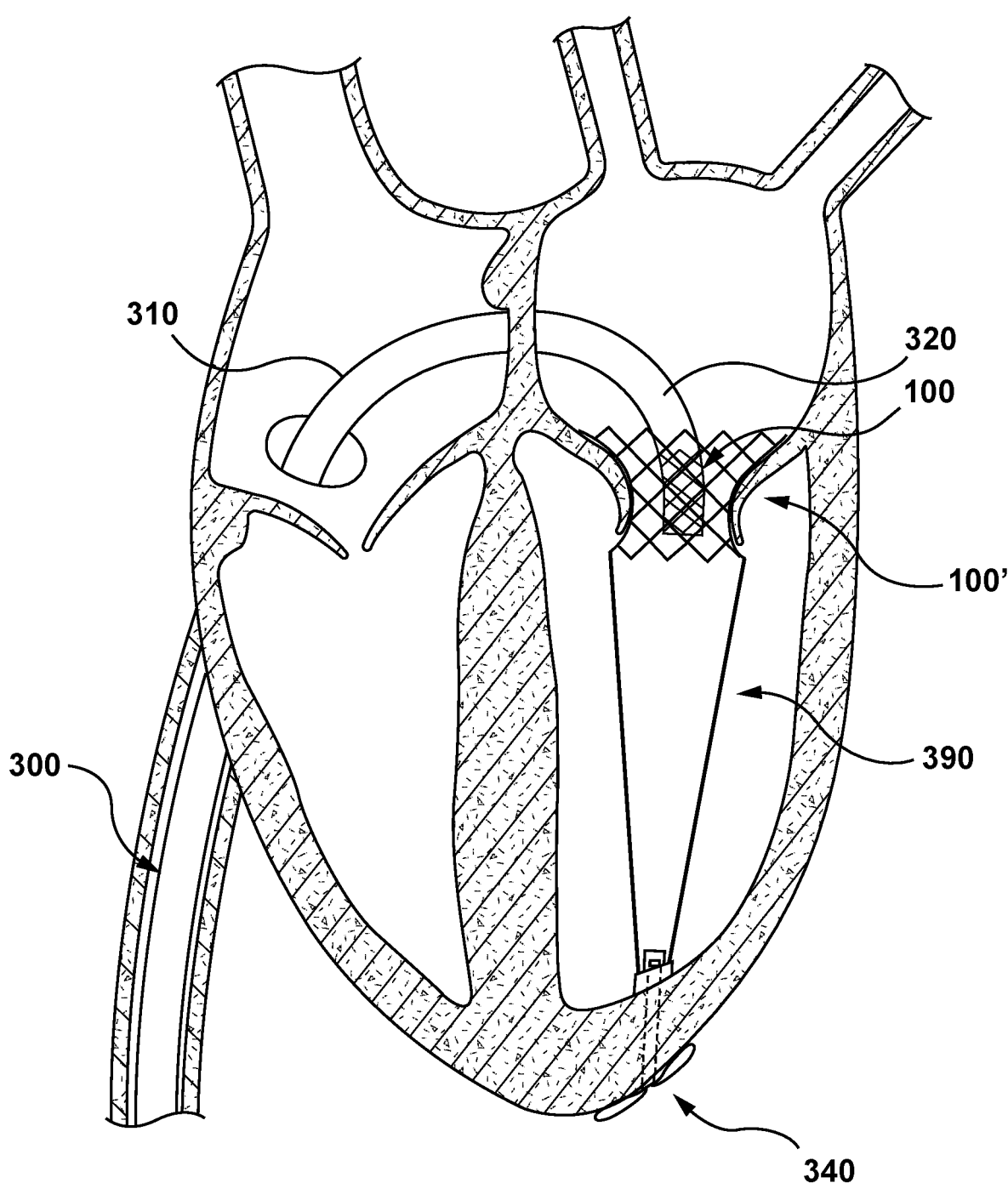
FIG. 27 is a sectional cutaway illustration of the heart illustrating a method step of using a delivery system to deliver and position a mitral valve prosthesis within a native mitral valve using a trans-septal approach, wherein the delivery system is advanced the mitral valve prosthesis is positioned within the docking stent at the annulus of the native mitral valve.
Figure 28:
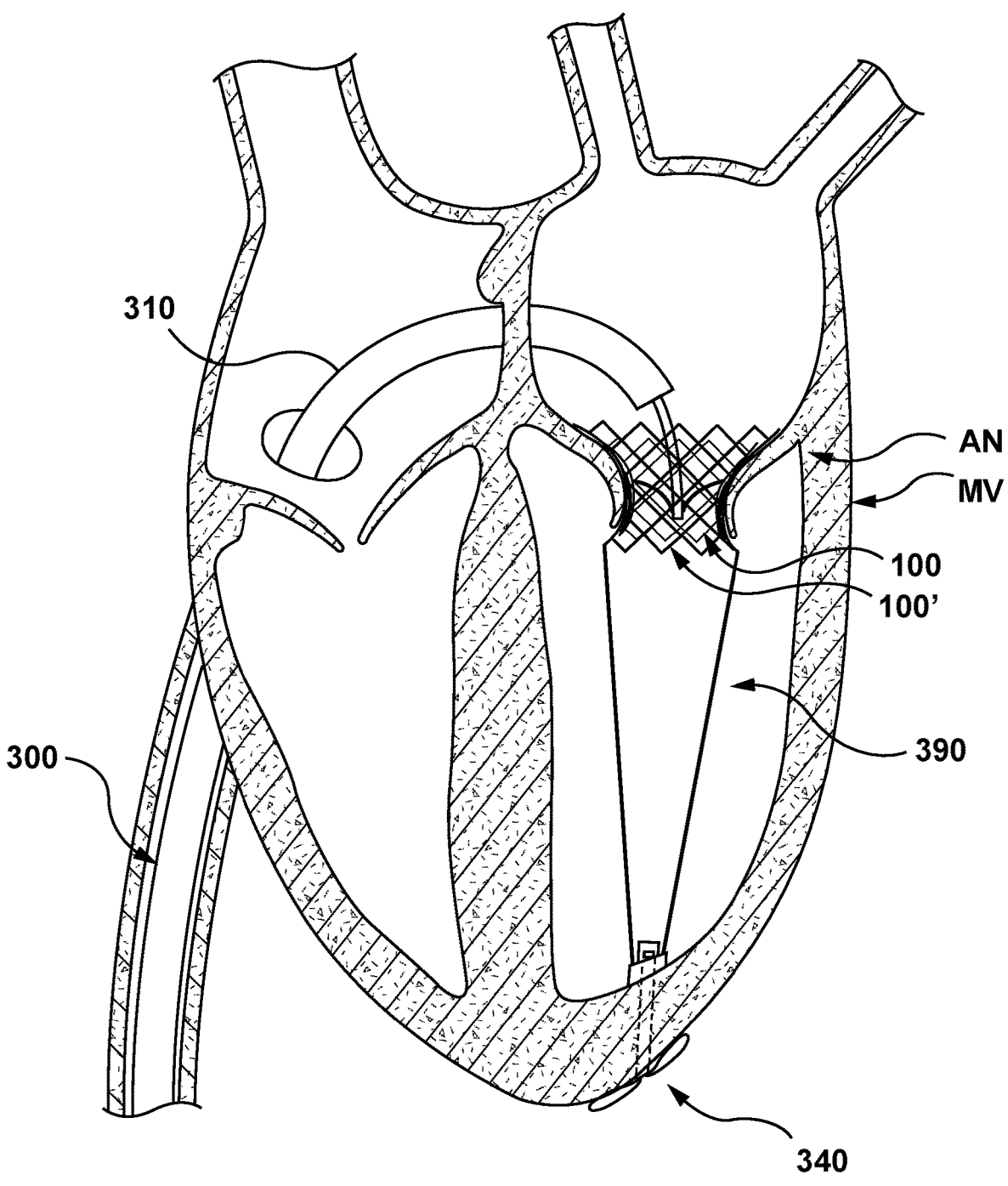
FIG. 28 is a sectional cutaway illustration of the heart illustrating a method step of using a delivery system to deliver and position a mitral valve prosthesis within a native mitral valve using a trans-septal approach, wherein the outer sheath of the delivery device is retracted to release the mitral valve prosthesis such that the mitral valve prosthesis expands to its radially expanded configuration within the docking stent at the annulus of the native mitral valve.

FIGS. 26-28 show schematically another embodiment of a method of replacing a mitral valve MV with a delivery system 300 of the present disclosure. Delivery system 300 is similar to delivery system 200 described previously. However, in the embodiment of FIGS. 26-28, delivery system 300 is configured to deliver and deploy a docking stent 100' prior to and in addition to stented prosthetic heart valve 100. Stented prosthetic heart valve 100 is disposed proximal of docking stent 100' in a radially collapsed configuration within an outer sheath 310 of delivery system 300. Therefore, details of the method up to and through the step of releasing a nosecone 340 from an inner shaft 320 will not be repeated.

With nosecone 340 coupled to delivery system 300 only by tether component 390, the clinician next retracts delivery system 300, as previously described and shown with reference to nosecone 240, inner shaft 220, and tether component 290 of delivery system 200 of FIG. 22. The clinician retracts delivery system 300 until tether component 390 is taut. Tautness of tether component 390 correctly positions docking stent 100' for deployment at the desired deployment site within annulus AN of mitral valve MV, as previously described and shown with reference to tether component 290 and stented prosthetic heart valve 100 of delivery system 200 of FIG. 23. With docking stent 100' properly aligned by tautness of tether component 390, the clinician retracts outer sheath 310 of delivery system 300 proximally, thereby releasing docking stent 100' disposed therein, and docking stent 100' expands radially to a radially expanded configuration at the desired deployment site. Upon expansion thereof, docking stent 100' engages an interior wall of annulus AN of mitral valve MV, as shown in FIG. 26.

With docking stent 100' properly deployed, the clinician advances delivery system 300 distally to a desired deployment site for stented prosthetic heart valve 100, within docking stent 100', as shown in FIG. 27. With stented prosthetic heart valve 100 properly aligned within previously expanded or deployed docking stent 100', the clinician retracts outer sheath 310 of delivery system 300 proximally, thereby releasing stented prosthetic heart valve 100 disposed therein, and stented prosthetic heart valve 100 expands radially to its radially expanded configuration at the desired deployment site. Upon expansion thereof, stented prosthetic heart valve 100 engages an interior wall of docking stent 100', as shown in FIG. 28.

With stented prosthetic heart valve 100 successfully deployed within docking stent 100' at annulus AN of mitral valve MV, delivery system 300 may be retracted and removed from the patient's vasculature using established procedures. Stented prosthetic heart valve 100 and docking stent 100' remain in the radially expanded configurations, as shown in FIG. 28. Docking stent 100' is anchored therein by nosecone 340 and taut tether component 390.

While the method of FIGS. 26-28 describe an embodiment of delivery system 300 containing both docking stent 100' and stented prosthetic heart valve 100, those skilled in the art will understand that docking stent 100' and stented prosthetic heart valve 100 may be deployed from separate delivery systems.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A method of positioning a valve prosthesis at a site of a native valve, wherein the native valve is a mitral valve, the method comprising the steps of:

advancing a delivery system through the native valve and into a chamber of the heart, wherein the delivery system includes a shaft, an anchoring component removably coupled to the shaft, the valve prosthesis disposed on a distal portion of the shaft in a radially collapsed configuration, and a tether component having a first end non-removably coupled to the anchoring component and a second end non-removably coupled to the valve prosthesis, wherein the step of advancing the delivery system through the native valve comprises advancing the delivery system through the mitral valve and into the left ventricle of the heart;

advancing the delivery system to a right atrium of the heart prior to the step of advancing the delivery system through the native valve;

advancing the delivery system through an interatrial septum to a left atrium of the heart;

advancing at least a portion of the anchoring component through the wall of the heart, wherein the step of advancing the anchoring component through the wall of the heart comprises advancing the anchoring component through a wall of the left ventricle;

positioning the anchoring component against an outer surface of the heart wall;

releasing the anchoring component from the delivery system; and deploying the valve prosthesis to a radially expanded configuration at the site of the native valve, wherein the valve prosthesis is deployed at a spaced apart location from the anchoring component and the tether component extends between the valve prosthesis deployed at the site of the native valve and the anchoring component positioned against the outer surface of the heart wall.

2. The method of claim 1, wherein the valve prosthesis is a stented prosthetic heart valve.

3. The method of claim 1, wherein the anchoring component is in a radially compressed configuration during the step of advancing the anchoring component through the wall of the heart.

4. The method of claim 3, further comprising the step of expanding the anchoring component to a radially expanded configuration after the step of advancing the anchoring component through the wall of the heart.

5. The method of claim 1, further comprising retracting the delivery system until the tether component becomes taut after the step of releasing the anchoring component from the delivery system.

6. The method of claim 1, wherein the anchoring component includes a plug that has a conical shape.

7. The method of claim 6, wherein the anchoring component is in a radially compressed configuration during the step of advancing the anchoring component through the wall of the heart and wherein the plug is stretched axially when the anchoring component is in the radially compressed configuration.

8. The method of claim 7, further comprising the step of expanding the anchoring component to a radially expanded configuration after the step of advancing the anchoring component through the wall of the heart, wherein the plug radially expands relative to the radially compressed configuration when the anchoring component is in the radially expanded configuration.

9. The method of claim 8, wherein the anchoring component includes a delivery configuration, and wherein a proximal portion of the plug has a first cross-sectional dimension when the anchoring component is in the radially compressed configuration, the proximal portion of the plug has a second cross-sectional dimension when the anchoring component is in the delivery configuration, and the proximal portion of the plug has a third cross-sectional dimension when the anchoring component is in the radially expanded configuration, wherein the third cross-sectional dimension is larger than the second cross-sectional dimension and the second cross-sectional dimension is larger than the first cross-sectional dimension.

10. The method of claim 1, wherein the tether component comprises a plurality of tethers and each tether is an elongate element.

11. The method of claim 1, wherein the delivery system further includes an outer sheath, the valve prosthesis being disposed within the outer sheath when in the radially collapsed configuration.

12. The method of claim 11, wherein the step of deploying the valve prosthesis includes retracting the outer sheath.

13. A method of positioning a prosthesis at a site of a native valve, the method comprising the steps of:

advancing a delivery system through the native valve and into a chamber of the heart, wherein the delivery system includes a shaft, an anchoring component removably coupled to the shaft, a prosthesis disposed on a distal portion of the shaft in a radially collapsed configuration, and a tether component having a first end non-removably coupled to the anchoring component and a second end non-removably coupled to the prosthesis, wherein the anchoring component forms a distal tip of the delivery system during the step of advancing the delivery system through the native valve;

advancing at least a portion of the anchoring component through the wall of the heart;

positioning the anchoring component against an outer surface of the heart wall;

releasing the anchoring component from the delivery system; and deploying the prosthesis to a radially expanded configuration at the site of the native valve, wherein the prosthesis is deployed at a spaced apart location from the anchoring component and the tether component extends between the prosthesis deployed at the site of the native valve and the anchoring component positioned against the outer surface of the heart wall.

14. The method of claim 13, wherein the prosthesis is a docking stent, further comprising the steps of:

after releasing the docking stent, positioning a stented prosthetic heart valve within the docking stent and deploying the stented prosthetic heart valve within the docking stent.

15. The method of claim 14, wherein the delivery system includes the stented prosthetic heart valve disposed therein, wherein the step of positioning the stented prosthetic heart valve within the docking stent comprises repositioning the delivery system, and wherein the step of deploying the stented prosthetic heart valve within the docking stent comprises releasing the stented prosthetic heart valve from the delivery system.

16. A method of positioning a valve prosthesis at a site of a native valve, wherein the native valve is a mitral valve, the method comprising the steps of:

advancing a delivery system through the native valve and into a chamber of the heart, wherein the delivery system includes a shaft, an anchoring component removably coupled to the shaft, the valve prosthesis disposed on a distal portion of the shaft in a radially collapsed configuration, and a tether component having a first end non-removably coupled to the anchoring component and a second end non-removably coupled to the valve prosthesis, wherein the step of advancing the delivery system through the native valve comprises advancing the delivery system through the mitral valve and into the left ventricle of the heart;

advancing the delivery system to a right atrium of the heart prior to the step of advancing the delivery system through the native valve;

advancing the delivery system through an interatrial septum to a left atrium of the heart;

advancing at least a portion of the anchoring component in a radially compressed configuration through the wall of the heart, wherein the step of advancing the anchoring component through the wall of the heart comprises advancing the anchoring component through a wall of the left ventricle;

positioning the anchoring component in a radially expanded configuration against an outer surface of the heart wall;

releasing the anchoring component from the delivery system; and deploying the valve prosthesis to a radially expanded configuration at the site of the native valve, wherein the valve prosthesis is deployed at a spaced apart location from the anchoring component and the tether component extends between the valve prosthesis deployed at the site of the native valve and the anchoring component positioned against the outer surface of the heart wall.

17. The method of claim 16, wherein the valve prosthesis is a stented prosthetic heart valve.

* * * * *